(12) United States Patent
Tsai

(10) Patent No.: US 9,649,304 B2
(45) Date of Patent: May 16, 2017

(54) SORBIC AND BENZOIC ACID AND DERIVATIVES THEREOF ENHANCE THE ACTIVITY OF A NEUROPHARMACEUTICAL

(75) Inventor: Guochuan Emil Tsai, Pasadena, CA (US)

(73) Assignee: Los Angeles Biomedical Research Institute at Harbor-UCLA Medical Center, Torrance, CA (US)

(*) Notice: Subject to any disclaimer, the term of this patent is extended or adjusted under 35 U.S.C. 154(b) by 153 days.

(21) Appl. No.: 12/689,957

(22) Filed: Jan. 19, 2010

(65) Prior Publication Data

US 2010/0189818 A1 Jul. 29, 2010

Related U.S. Application Data

(60) Provisional application No. 61/145,931, filed on Jan. 20, 2009.

(51) Int. Cl.

| | | |
|---|---|---|
| A01N 59/00 | (2006.01) |
| A61K 33/00 | (2006.01) |
| A61K 31/47 | (2006.01) |
| A61K 31/11 | (2006.01) |
| A61K 31/12 | (2006.01) |
| A61K 31/13 | (2006.01) |
| A61K 31/16 | (2006.01) |
| A61K 31/19 | (2006.01) |
| A61K 31/192 | (2006.01) |
| A61K 31/22 | (2006.01) |
| A61K 31/235 | (2006.01) |
| A61K 31/245 | (2006.01) |
| A61K 31/35 | (2006.01) |
| A61K 31/382 | (2006.01) |
| A61K 31/5513 | (2006.01) |
| A61K 36/16 | (2006.01) |
| A61K 45/06 | (2006.01) |
| A61K 31/196 | (2006.01) |
| A61K 31/167 | (2006.01) |

(52) U.S. Cl.
CPC ............ *A61K 31/47* (2013.01); *A61K 31/11* (2013.01); *A61K 31/12* (2013.01); *A61K 31/13* (2013.01); *A61K 31/16* (2013.01); *A61K 31/167* (2013.01); *A61K 31/19* (2013.01); *A61K 31/192* (2013.01); *A61K 31/196* (2013.01); *A61K 31/22* (2013.01); *A61K 31/235* (2013.01); *A61K 31/245* (2013.01); *A61K 31/35* (2013.01); *A61K 31/382* (2013.01); *A61K 31/5513* (2013.01); *A61K 33/00* (2013.01); *A61K 36/16* (2013.01); *A61K 45/06* (2013.01)

(58) Field of Classification Search
None
See application file for complete search history.

(56) References Cited

U.S. PATENT DOCUMENTS

| | | |
|---|---|---|
| 3,498,989 A | 3/1970 | Sallay et al. |
| 3,870,715 A | 3/1975 | Hansl |
| 4,041,174 A | 8/1977 | Sapse |
| 4,956,363 A | 9/1990 | Wulfert et al. |
| 5,453,425 A | 9/1995 | Francois et al. |
| 5,616,587 A * | 4/1997 | Fran.cedilla.ois et al. ........................ 514/259.41 |
| 5,658,900 A | 8/1997 | Boireau et al. |
| 6,569,848 B1 | 5/2003 | Davis et al. |
| 6,746,678 B1 | 6/2004 | Shapiro |
| 7,094,930 B2 | 8/2006 | Quallich et al. |
| 7,166,725 B2 | 1/2007 | Fang et al. |
| 2001/0044446 A1* | 11/2001 | Phillips et al. ............... 514/282 |
| 2003/0185754 A1* | 10/2003 | Cohen et al. .................. 424/9.2 |

(Continued)

FOREIGN PATENT DOCUMENTS

| | | |
|---|---|---|
| DE | 4340273 A1 | 6/1995 |
| WO | WO02066672 A2 | 8/2002 |

(Continued)

OTHER PUBLICATIONS

"Structure-Activity Relationship and Drug Design." Remington's Pharmaceutical Sciences (Sixteenth Edition). Mack Publishing. 1980. pp. 420-425.*
Wilhelm et al. Flavoenzyme catalysis. Substrate-competitive inhibition of D-amino acid oxidase. Journal of Biological Chemistry, 223, 75-83, 1956.*
"Structure-Activity Relationship and Drug Design." Remington's Pharmaceutical Sciences (Sixteenth Edition). Mack Publishing, 1980, pp. 420-425.*

(Continued)

*Primary Examiner* — Dennis Heyer
*Assistant Examiner* — Daniel M Podgorski
(74) *Attorney, Agent, or Firm* — Wolf, Greenfield & Sacks, P.C.

(57) ABSTRACT

Methods and compositions are provided for treating neuropsychiatric disorders such as schizophrenia, depression, attention deficit disorder, mild cognitive impairment, dementia, and bipolar disorder. The methods entail administering to a patient diagnosed as having a neuropsychiatric disorder (e.g., schizophrenia, depression, attention deficit disorder, mild cognitive impairment, dementia bipolar disorder, etc.) or as at risk for a neuropsychiatric disorder a benzoic acid, benzoic acid salt, and/or benzoic acid derivative, and/or a sorbic acid, sorbic acid salt, and/or sorbic acid derivative, in combination with a neuropharmacological agent (e.g., an antipsychotic, an antidepressant, medications for attention deficit and hyperactivity disorder, cognitive impairment, or dementia, etc.) where the benzoic acid, benzoic acid salt, or benzoic acid derivative, and/or a sorbic acid, sorbic acid salt, and/or sorbic acid derivative, is in an amount sufficient to increase the efficacy of the neuropharmacological agent.

7 Claims, 3 Drawing Sheets

(56) References Cited

U.S. PATENT DOCUMENTS

| | | |
|---|---|---|
| 2004/0138197 A1 | 7/2004 | Maw et al. |
| 2004/0138298 A1* | 7/2004 | Mermelstein et al. ....... 514/474 |
| 2005/0272721 A1 | 12/2005 | Keltjens |
| 2008/0045512 A1 | 2/2008 | Duplantier et al. |

FOREIGN PATENT DOCUMENTS

| | | |
|---|---|---|
| WO | WO2005000205 A2 | 6/2005 |
| WO | WO2005117911 A2 | 12/2005 |
| WO | WO 2006/129160 * | 12/2006 |
| WO | WO2007093829 A1 | 8/2007 |

OTHER PUBLICATIONS

Berge et al. "Pharmaceutical Salts." Journal of Pharmaceutical Sciences, 66(1); 1977: 1-19.*

Dorwald. Side reactions in organic synthesis. 2006.*

McCracken et al. Risperidone in children with autism and serious behavioral problems. N. Eng. J. Med. vol. 347, No. 5, Aug. 1, 2002.*

Adage et al., "In vitro and in vivo pharmacological profile of AS057278, a selective d-amino acid oxidase inhibitor with potential anti-psychotic properties", Mar. 2008, pp. 200-214, Eur Neuropsychopharmacol.

Millian et al., "Overview of drug classes proposed for the treatment of cognitive impairments in psychiatric disorders", table 2, Feb. 2012, pp. 1-7, www.nature.com/nrd/journal/v11/n2/fig_tab/nrd3628_T2.html.

Smith et al., "The Therapeutic Potential of D-Amino Acid Oxidase (DAAO) Inhibitors", 2010, vol. 4, pp. 3-9, The Open Medicinal Chemistry Journal.

Tsai et al., "Strategies to Enhance N-Methyl-D-Aspartate Receptor-Mediated Neurotransmission in Schizophrenia, a Critical Review and Meta-Analysis", 2010, vol. 16, pp. 1-16.

Zhu Yi-bing et al., "Investigation of the Therapy of TD with ADHD", Department of Pediatrics of Shanghai Baoshan Centre Hospital, Shanghai, China, Guide of China Medicine, Oct. 2008, vol. 6, No. 19, pp. 1-7.

Zhao et al.; Inhibition of D-Amino-Acid Oxidase Activity Induces Pain Relief in Mice; Cell Mol Neurobiol (2008) 28:581-591.

Gaisler-Salomon et al. "Abnormally persistent latent inhibition induced by MK801 is reversed by risperidone and by positive modulators of NMDA receptor function: differential efficacy depending on the stage of the task at which they are administered", Psychopharmacology (2008) 196:255-267.

Ishiyama et al. "Lurasidone (SM-13496), a novel atypical antipsychotic drug, reverses MK-801-induced impairment of learning and memory in the rat passive-avoidance test", European Journal of Pharmacology 572 (2007) pp. 160-170.

Matin et al. "Dextromethorphan-Induced Near-Fatal Suicide Attempt in a Slow Metabolizer at Cytochrome P450 2D6", The American Journal of Geriatric Pharmacotherapy, vol. 5, No. 2, Jun. 2007, pp. 162-165.

McLean et al. "A preliminary investigation into the effects of antipsychotics on sub-chronic phencyclidine-induced deficits in attentional set-shifting in female rats", Behavioral Brain Research 189 (2008) pp. 152-158.

Su et al. "Risperidone attenuates MK-801-induced hyperlocomotion in mice via the blockade of serotonin 5-HT2A/2C receptors", European Journal of Pharmacology 654 (2007) pp. 123-130.

* cited by examiner

SORBIC AND BENZOIC ACID AND DERIVATIVES THEREOF ENHANCE THE ACTIVITY OF A NEUROPHARMACEUTICAL

CROSS-REFERENCE TO RELATED APPLICATIONS

This application claims benefit of and priority to U.S. Ser. No. 61/145,931, filed on Jan. 20, 2009, which is incorporated herein by reference in its entirety for all purposes.

STATEMENT AS TO RIGHTS TO INVENTIONS MADE UNDER FEDERALLY SPONSORED RESEARCH AND DEVELOPMENT

[Not Applicable]

FIELD OF THE INVENTION

This is invention pertains the field of neuropsychiatry. In particular treatment methods are provided for neuropsychiatric disorders.

BACKGROUND OF THE INVENTION

Schizophrenia, Alzheimer's Disease, autism, depression, benign forgetfulness, childhood learning disorders, close head injury, and attention deficit disorder (ADD), dementia, mild cognitive impairment, ataxia, spinocerebellar degeneration, Parkinson's disease, obsessive compulsive disorder (OCD), substance abuse, and substance dependence are examples of neuropsychiatric disorders. Autism, for example, is a developmental mental disorder characterized by autistic behavior, social failure, and language delay. Alzheimer's Disease is a form of dementia that typically involves progressive mental deterioration, manifested by memory loss, confusion, and disorientation. Alzheimer's Disease typically is treated by acetylcholine esterase inhibitors such as tacrine hydrochloride or donepezil. Attention Deficit Disorder is a disorder that is most prevalent in children and is associated with increased motor activity and a decreased attention span. Attention Deficit Disorder commonly is treated by administration of psychostimulants or other medications such as Ritalin, Dexedrin, or atomoxetin. Depression is a clinical syndrome that includes a persistent sad mood or loss of interest in activities, which persists for at least two weeks in the absence of treatment. Conventional therapeutics include serotonin uptake inhibitors (e.g., PROZAC®), monoamine oxidase inhibitors, and tricyclic antidepressants.

The term schizophrenia represents a group of neuropsychiatric disorders characterized by dysfunctions of the thinking process, such as delusions, hallucinations, and extensive withdrawal of the patient's interests from other people. Approximately one percent of the worldwide population is afflicted with schizophrenia, and this disorder is accompanied by high morbidity and mortality rates.

Conventional antipsychotic drugs, which act on the dopamine $D_2$ receptor, can be used to treat the positive symptoms of schizophrenia, such as delusion and hallucination. In general, conventional antipsychotic drugs and the new atypical antipsychotic drugs, which act on the dopamine $D_2$ and 5HT2 serotonin receptor, are limited in their ability to treat cognitive deficits and negative symptoms such as affect blunting (i.e., lack of facial expressions), anergia, and social withdrawal.

SUMMARY OF THE INVENTION

In certain embodiments this invention pertains to "combination" pharmaceutical compositions comprising a benzoic acid, benzoic acid salt, benzoic acid ester or other benzoic acid derivative, and/or a sorbic acid, sorbic acid salt, sorbic acid ester, or other sorbic acid derivative and a neuropharmaceutical (e.g., an antipsychotic drug (e.g., risperidone, olanzapine, etc.), and antidepressant (e.g., sertraline, fluoxetine hydrochloride, etc.), a psychotropic medication for attention deficit and hyperactivity disorder (e.g., Ritalin, Dexedrine, Atomoxetine, etc.), a psychotropic medication for dementia (e.g., Aricept, memantine), and the like). Typically, the benzoic acid, benzoic acid salt, benzoic acid ester or other benzoic acid derivative, and/or a sorbic acid, sorbic acid salt, sorbic acid ester, or other sorbic acid derivative is present in an amount sufficient to increase the efficacy of the neuropharmaceutical. In certain embodiments the benzoic acid is provided as a benzoic acid salt (e.g. sodium benzoate, potassium benzoate, calcium benzoate, etc.). In certain embodiments the benzoic acid, benzoic acid salt, or derivative thereof is selected from the group consisting of benzoic acid, sodium benzoate, potassium benzoate, calcium benzoate, 2-aminobenzoate, 3-aminobenzoate, and 4-aminobenzoate. In certain embodiments the sorbic acid is provided as a sorbic acid salt (e.g., sodium sorbate, potassium sorbate, calcium sorbate, etc.). In certain embodiments the sorbic acid, sorbic acid salt, sorbic acid ester, and/or sorbic acid derivative is selected from the group consisting of sorbic acid, sodium sorbate, potassium sorbate, calcium sorbate, sorbohydroxamic acid, a sorbic aldehyde, a sorbic acid-thiol adduct, 8-quinolinylsorbate, and m-nitrosorbanilide.

In certain embodiments the ratio of benzoic acid, benzoic acid salt, or benzoic acid derivative and/or sorbic acid, sorbic acid salt, or sorbic acid derivative to neuropharmaceutical is stoichiometrically greater than 2:1, greater than 3:1, greater than 4:1 greater than 5:1, greater than 6:1, greater than 7:1, greater than 8:1, greater than 9:1, or greater than 10:1 or 20:1.

In certain embodiments the neuropharmaceutical is selected from the group consisting of an antidepressant, an antipsychotic, a phsycostimulant, a mood stabilizer, an anxiolytic, an ADHD therapeutic, and an Alzheimer's disease therapeutic. In certain embodiments the neuropharmaceutical is an antipsychotic drug (e.g., butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupenthixol, thiothixene, zuclopenthixol, clozapine, olanzapine, risperidone, quetiapine, ziprasidone, amisulpride, asenapine, paliperidone, aripiprazole, a dopamine partial agonist, lamotrigine, memantine, tetrabenazine, cannabidiol, and/or LY2140023). In certain embodiments the neuropharmaceutical is an antidepressant drug (e.g., a monoamine oxidase inhibitor (MAOI), a tricyclic antidepressant (TCA), a tetracyclic antidepressant (TeCA), a selective serotonin reuptake inhibitor (SSRI), and a serotonin-norepinephrine reuptake inhibitor (SNRI). In certain embodiments the neuropharmaceutical is an ADHD medication (e.g., Ritalin, Dexedrine, Atomoxetine, and the like). In certain embodiments the neuropharmaceutical is a medication for improving cognition and/or inhibiting neurodegeneration (e.g., Aricept. memantine, etc.).

Also provided are methods for mitigating one or more symptoms of a neuropsychiatric disorder (e.g., schizophrenia, depression, attention deficit disorder, mild cognitive impairment, dementia, attention deficit hyperactivity disorder (ADHD), bipolar disorder, and the like). The methods typically involve administering to a subject in need thereof a benzoic acid, benzoic acid salt, or benzoic acid derivative and/or a sorbic acid, sorbic acid salt, or sorbic acid derivative in an amount sufficient to mitigate one or more symptoms of a neuropsychiatric disorder. In certain embodiments the method comprises administering to the subject the benzoic acid, benzoic acid salt, or benzoic acid derivative and/or a sorbic acid, sorbic acid salt, or sorbic acid derivative in conjunction with a neuropharmaceutical, where the benzoic acid, benzoic acid salt, or benzoic acid derivative and/or a sorbic acid, sorbic acid salt, or sorbic acid derivative is administered in an amount sufficient to increase the efficacy of the neuropharmaceutical. In certain embodiments the benzoic acid, benzoic acid salt, benzoic acid ester, or derivative thereof and/or a sorbic acid, sorbic acid salt, sorbic acid ester, or derivative thereof and the neuropharmaceutical are administered simultaneously (i.e., separately or in a combined formulation). In certain embodiments the benzoic acid, benzoic acid salt, benzoic acid ester, or derivative thereof and/or a sorbic acid, sorbic acid salt, sorbic acid ester, or derivative thereof is administered before or after the neuropharmaceutical.

In certain embodiments of the methods, the benzoic acid is provided as a benzoic acid salt (e.g. sodium benzoate, potassium benzoate, calcium benzoate, etc.). In certain embodiments the benzoic acid, benzoic acid salt, or derivative thereof is selected from the group consisting of benzoic acid, sodium benzoate, potassium benzoate, calcium benzoate, 2-aminobenzoate, 3-aminobenzoate, and 4-aminobenzoate. In certain embodiments the sorbic acid is provided as a sorbic acid salt (e.g., sodium sorbate, potassium sorbate, calcium sorbate, etc.). In certain embodiments the sorbic acid, sorbic acid salt, sorbic acid ester, and/or sorbic acid derivative is selected from the group consisting of sorbic acid, sodium sorbate, potassium sorbate, calcium sorbate, sorbohydroxamic acid, a sorbic aldehyde, a sorbic acid-thiol adduct, 8-quinolinylsorbate, and m-nitrosorbanilide.

In certain embodiments of the methods, the ratio of benzoic acid, benzoic acid salt, or benzoic acid derivative and/or sorbic acid, sorbic acid salt, or sorbic acid derivative to neuropharmaceutical is stoichiometrically greater than 2:1, greater than 3:1, greater than 4:1 greater than 5:1, greater than 6:1, greater than 7:1, greater than 8:1, greater than 9:1, or greater than 10:1 or 20:1.

In certain embodiments of the methods, the neuropharmaceutical is selected from the group consisting of an antidepressant, an antipsychotic, a psychostimulant, a mood stabilizer, an anxiolytic, an ADHD therapeutic, and an Alzheimer's disease therapeutic. In certain embodiments the, the neuropsychiatric disorder is schizophrenia and/or bipolar disorder, and the neuropharmaceutical is an antipsychotic drug (e.g., butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupenthixol, thiothixene, zuclopenthixol, clozapine, olanzapine, risperidone, quetiapine, ziprasidone, amisulpride, asenapine, paliperidone, aripiprazole, a dopamine partial agonist, lamotrigine, memantine, tetrabenazine, cannabidiol, and/or LY2140023). In certain embodiments the, the neuropsychiatric disorder is depression, and the neuropharmaceutical is an antidepressant drug (e.g., a monoamine oxidase inhibitor (MAOI), a tricyclic antidepressant (TCA), a tetracyclic antidepressant (TeCA), a selective serotonin reuptake inhibitor (SSRI), and a serotonin-norepinephrine reuptake inhibitor (SNRI). In certain embodiments, the neuropsychiatric disorder is ADHD and the neuropharmaceutical is an ADHD medication (e.g., ritalin, dexedrine, atomoxetine, and the like). In certain embodiments, the neuropsychiatric disorder is characterized by loss in cognition and/or neurodegeneration (e.g. Alzheimer's disease), and the neuropharmaceutical is a medication for improving cognition and/or inhibiting neurodegeneration (e.g., Aricept. memantine, etc.). In various embodiments of the methods, the subject is a human diagnosed having or as at risk for a neuropsychiatric disorder. In various embodiments the subject is a non-human mammal (e.g., a canine, a feline, an equine, etc.). In various embodiments the methods are performed prophylactically, or therapeutically.

Uses for benzoic acid, benzoic acid salt, or benzoic acid derivative and/or a sorbic acid, sorbic acid salt, or sorbic acid derivative as active agents in the manufacture of medicaments for the treatment of a neuropsychiatric disorder are provided where the benzoic acid, benzoic acid salt, benzoic acid ester, or benzoic acid derivative and/or a sorbic acid, sorbic acid salt, sorbic acid ester or sorbic acid derivative is present in an amount effective to mitigate one or more symptoms of the neuropsychiatric disorder are also provided. Similarly, uses for benzoic acid, benzoic acid salt, or benzoic acid derivative and/or a sorbic acid, sorbic acid salt, or sorbic acid derivative in combination with a neuropharmaceutical in the manufacture of a medicament for the treatment of a neuropsychiatric disorder, where the benzoic acid, benzoic acid salt, or benzoic acid derivative and/or a sorbic acid, sorbic acid salt, or sorbic acid derivative is present in an amount sufficient to increase the efficacy of the neuropharmaceutical are provided. In various embodiments the benzoic acid, benzoic acid salt, benzoic acid ester, and/or benzoic acid derivative is a benzoic acid salt. In various embodiments the benzoic acid, benzoic acid salt, benzoic acid ester, and/or benzoic acid derivative is selected from the group consisting of benzoic acid, sodium benzoate, potassium benzoate, calcium benzoate, 2-aminobenzoate, 3-aminobenzoate, and 4-aminobenzoate. In various embodiments the sorbic acid, sorbic acid salt, sorbic acid ester, and/or sorbic acid derivative is a sorbic acid salt. In certain embodiments the sorbic acid, sorbic acid salt, sorbic acid ester, and/or sorbic acid derivative is selected from the group consisting of sorbic acid, sodium sorbate, potassium sorbate, calcium sorbate, sorbohydroxamic acid, a sorbic aldehyde, a sorbic acid-thiol adduct, 8-quinolinylsorbate, and m-nitrosorbanilide. In various embodiments the neuropharmaceutical, when present, includes any one or more of the neuropharmaceuticals described herein.

In certain embodiments this invention pertains to the discovery that administration of any two or all three of (i) an NMDA (N-methyl-D-aspartate)-Enhancer, and/or (ii) a glycine transporter inhibitor, and/or (iii) a D-amino Acid Oxidase Inhibitor (DAAOI) to a subject having or at high risk for a neuropsychiatric disorder, provides substantially greater efficacy at reducing or eliminating symptoms of the disorder than previously known single-agent therapeutic regimes. In various embodiments, this invention also provides pharmacological compositions comprising any two or all three agents in combination and methods utilizing such combined formulations.

Accordingly in certain embodiments, a pharmaceutical composition (and method of use thereof) is provided where the composition comprises a D-amino Acid Oxidase Inhibitor (DAAOI) (e.g., benzoic acid, benzoic acid salt, benzoic acid derivative and/or a sorbic acid, sorbic acid salt, or sorbic acid derivative) and/or an NMDA enhancer and/or a glycine transporter inhibitor. In certain embodiments, a pharmaceutical composition is provided where the composition comprises a benzoic acid, benzoic acid salt, or benzoic acid derivative and/or a sorbic acid, sorbic acid salt, or sorbic acid derivative; and an NMDA enhancer. In certain embodiments, a pharmaceutical composition is provided where the composition comprises a benzoic acid, benzoic acid salt, or benzoic acid derivative and/or a sorbic acid, sorbic acid salt, or sorbic acid derivative; and a glycine transporter inhibitor. In certain embodiments, a pharmaceutical composition is provided where the composition comprises a benzoic acid, benzoic acid salt, or benzoic acid derivative and/or a sorbic acid, sorbic acid salt, or sorbic acid derivative; an NMDA enhancer; and a glycine transporter inhibitor. In various embodiments of these compositions, the D-amino Acid Oxidase Inhibitor comprises benzoic acid, benzoic acid salt, or benzoic acid derivative and/or a sorbic acid, sorbic acid salt, or sorbic acid derivative alone together with each other, or alone or together with each other and an additional DAAO inhibitor described herein. In various embodiments the NMDA enhancer, when present, comprises one or more NMDA enhancers described herein. In various embodiments the glycine transporter inhibitor, when present comprises one or more glycine transporter inhibitors described herein.

In various embodiments these compositions comprise an additional neuropharmaceutical, e.g., an antipsychotic, an antidepressant, a psychostimulant, a mood stabilizer, an anxiolytic, an Alzheimer's disease therapeutic, and/or other psychotropic. In certain embodiments the additional therapeutic agent is one or more agents selected from the neuropharmaceuticals described herein (e.g., diazepam, bromazepam, prazepam, chlordiazepoxide, clobazam, estazolam, flurazepam, clonazepam, temazepam, triazolam, alprazolam, midazolam, brotizolam, nitrazepam, flunitrazepam, oxazepam, quazepam, lorazepam, temazepam, triazolam, zolpidem, zopiclone, zaleplon, chlorpromazine, thioridazine, mesoridazine, fluphenazine, perphenazine, trifluoperazine, thiothixene, haloperidol, loxapine, molindone, clozapine, risperidone, olanzapine, quetiapine, haloperidol decanoate, fluphenazine decanoate, fluphenazine enanthate, risperdal consta, sulpiride, ziprasidone, aripiprazole, paliperidone, acetophenazine, chlorprothixene, droperidol, pimozide, butaperazine, carphenazine, remoxipride, piperacetazine, amitriptyline, imipramine, nortriptiline, protriptyline, desipramine, trimipramine, amoxapine, bupropion, bupropion sr, citalopram, s-citalopram, clomipramine, desipramine, doxepin, duloxetine, milnacipran, fluoxetine, fluvoxamine, imipramine, isocarboxazid, isoniazid, iproniazid, fluoxetine, paroxetine, sertraline fluvoxamine, venlafaxine, velafaxine xr, milnacipram and duloxetine, mirtazapine, mianserin, reboxetine, selegiline, tranylcypromine, trazodone, nefazodone, phenelzine, lamatrogine, lithium, topiramate, gabapentin, carbamazepine, oxacarbazepine, valporate, maprotiline, mirtazapine, brofaromine, gepirone, moclobemide, physostigmine, nicotine, huperzine alpha, vitamine c, vitamine, carotenoids, *ginkgo biloba*, statinsamphetamine, modafinil, desoxyn, methamphetamine, cocaine, arecoline, dexmethylphenidate, dextroamphetamine, methylphenidate, lisdexamfetamine dimesylate (vyvanse), mixed salts amphetamine, atomoxetine, clonidine hydrochloride, guanfacine hydrochloride, arecoline, pemoline, donepezil, tacrine, rivastigmine, memantine, lamotrigine, acamprosate, tetrabenazine, riluzole).

In certain embodiments any of the compositions described herein is formulated as a unit dosage formulation. In certain embodiments the active agent(s) comprising the composition are independently formulated as salts, esters, or prodrugs. In certain embodiments the composition is formulated for administration by a route selected from the group consisting of oral administration, transdermal administration, transnasal administration, intramuscular administration, rectal administration, intravenous administration, intrathecal administration, intraperitoneal administration, administration in a subcutaneous depot formulation, and administration as an inhalant.

Also provided are methods of mitigating one or more symptoms of a neuropsychiatric disorder. The methods typically involve administering to a subject in need thereof a benzoic acid, benzoic acid salt, or benzoic acid derivative and/or a sorbic acid, sorbic acid salt, or sorbic acid derivative in conjunction with an NMDA enhancer and/or a glycine transporter inhibitor. In certain embodiments the composition comprises any of the drug combinations described herein. In certain embodiments the neuropsychiatric disorder is schizophrenia. In certain embodiments the neuropsychiatric disorder is bipolar disorder or mania, or hypomania. In certain embodiments the neuropsychiatric disorder is mild cognitive impairment, Alzheimer's disease and/or Parkinson's disease and/or dementia. In certain embodiments the neuropsychiatric disorder is ataxia and/or spinocerebellar degeneration. In certain embodiments the neuropsychiatric disorder is autism or Asperger's disorder. In certain embodiments the neuropsychiatric disorder is depression or dysthymia. In certain embodiments the neuropsychiatric disorder is benign forgetfulness or mild cognitive impairment. In certain embodiments the neuropsychiatric disorder is a childhood learning disorder (e.g., attention deficit disorder). In certain embodiments the neuropsychiatric disorder is close head injury. In certain embodiments the neuropsychiatric disorder is anxiety disorders including obsessive compulsive disorder, generalized anxiety disorder, panic disorder, phobia, social phobia. In certain embodiments the neuropsychiatric disorder is close post-traumatic stress disorder. In certain embodiments the neuropsychiatric disorder is substance abuse and/or substance dependence.

In certain embodiments any of the uses and/or methods described herein expressly exclude one or more neuropsychiatric disorders selected from the group consisting of schizophrenia, bipolar disorder, Alzheimer's disease, Parkinson's disease, dementia, ataxia, spinocerebellar degeneration, ADD, ADHD, depression, and mild cognitive impairment. In certain embodiments the use benzoic acid, salt, ester, or other benzoic acid derivative and/or sorbic acid, salt, ester, or other sorbic acid derivative in the treatment of neurodegenerative conditions (e.g., Alzheimer's disease, senile dementia of the Alzheimer type, etc.) is excluded. In certain embodiments the use benzoic acid, salt, ester, or other benzoic acid derivative in the treatment of neurodegenerative conditions (e.g., Alzheimer's disease, senile dementia of the Alzheimer type, etc.) is excluded.

DEFINITIONS

As used herein, the term "neuropsychiatric disorder" refers to a disease having a pathophysiological component of attenuated NMDA receptor-mediated neurotransmission. Examples of such disorders include schizophrenia, bipolar disorder, Alzheimer's disease, dementia, autism, Asperger's disorder, depression, benign forgetfulness, mild cognitive impairment, childhood learning disorders, close head injury, ataxia, spinocerebellar degeneration, Parkinson's disease, general anxiety disorder, panic disorder, obsessive compulsive disorder, phobia including social phobia, substance abuse, substance dependence, and attention deficit disorder.

As used herein, the term "schizophrenia" refers to a psychiatric disorder that includes at least two of the following: delusions, hallucinations, disorganized speech, grossly disorganized or catatonic behavior, or negative symptoms. Patients can be diagnosed as schizophrenic using the DSMIV criteria (APA, 1994, Diagnostic and Statistical Manual of 30 Mental Disorders (Fourth Edition), Washington, D.C.).

Bipolar disorder or manic-depressive disorder (also referred to a bipolarism or manic depression) is a psychiatric diagnosis that describes a category of mood disorders defined by the presence of one or more episodes of abnormally elevated mood clinically referred to as mania or, if milder, hypomania. Individuals who experience manic episodes also commonly experience depressive episodes or symptoms, or mixed episodes in which features of both mania and depression are present at the same time. These episodes are usually separated by periods of "normal" mood, but in some individuals, depression and mania may rapidly alternate, known as rapid cycling. Extreme manic episodes can sometimes lead to psychotic symptoms such as delusions and hallucinations. The disorder has been subdivided into bipolar I, bipolar II, cyclothymia, and other types, based on the nature and severity of mood episodes experienced; the range is often described as the bipolar spectrum. Patients can be diagnosed as having bipolar disorder using the DSMIV criteria.

The term "Alzheimer's Disease" refers to a progressive mental deterioration manifested by memory loss, confusion and disorientation beginning in late middle life and typically resulting in death in five to ten years. Pathologically, Alzheimer's Disease can be characterized by thickening, conglutination, and distortion of the intracellular neurofibrils, neurofibrillary tangles and senile plaques composed of granular or filamentous argentophilic masses with an amyloid core. Methods for diagnosing Alzheimer's Disease are known in the art. For example, the National Institute of Neurological and Communicative Disorders and Stroke-Alzheimer's Disease—and the Alzheimer's Disease and Related Disorders Association (NINCDS-ADRDA) criteria can be used to diagnose Alzheimer's Disease (McKhann et al. (1984) *Neurology* 34: 939-944). The patient's cognitive function can be assessed by the Alzheimer's Disease Assessment Scale-cognitive subscale (ADAS-cog; Rosen et al. (1984) *Am. J. Psychiatry* 141: 1356-1364).

Dementia is the progressive decline in cognitive function due to damage or disease in the brain beyond what might be expected from normal aging. Patients can be diagnosed as suffering from dementia by using the DSM-IV criteria. Dementia also includes mild cognitive impairment (MCI, also known as incipient dementia, or isolated memory impairment) which is a diagnosis given to individuals who have cognitive impairments beyond that expected for their age and education, but that do not interfere significantly with their daily activities. It is considered to be the boundary or transitional stage between normal aging and dementia. These individuals tend to progress to probable Alzheimer's disease at a rate of approximately 10% to 15% per year. Additionally, when individuals have impairments in domains other than memory it is classified as non-amnestic single- or multiple-domain MCI and these individuals are believed to be more likely to convert to other dementias (i.e. dementia with Lewy bodies).

As used herein, the term "autism" refers to a state of mental introversion characterized by morbid self-absorption, social failure, language delay, and stereotyped behavior. Patients can be diagnosed as suffering from autism by using the DSM-IV criteria.

Asperger's disorder (syndrome) is an autism spectrum disorder, and people with it therefore show significant difficulties in social interaction, along with restricted and repetitive patterns of behavior and interests. It differs from other autism spectrum disorders by its relative preservation of linguistic and cognitive development. Although not required for diagnosis, physical clumsiness and atypical use of language are frequently reported. Patients can be diagnosed as suffering from Asperger's disorder by using the DSM-IV criteria.

As used herein, the term "depression" refers to a clinical syndrome that includes a persistent sad mood or loss of interest in activities, which lasts for at least two weeks in the absence of treatment. The DSM-IV criteria can be used to diagnose patients as suffering from depression.

The term "benign forgetfulness," as used herein, refers to a mild tendency to be unable to retrieve or recall information that was once registered, learned, and stored in memory (e.g., an inability to remember where one placed one's keys or parked one's car). Benign forgetfulness typically affects individuals after 40 years of age and can be recognized by standard assessment instruments such as the Wechsler Memory Scale (Russell (1975) *J. Consult Clin. Psychol.* 43: 800-809).

As used herein, the term "childhood learning disorders" refers to an impaired ability to learn, as experienced by certain children. Such learning disorders can be diagnosed by using the DSM-IV criteria.

The term "close head injury," as used herein, refers to a clinical condition after head injury or trauma which condition can be characterized by cognitive and memory impairment. Such a condition can be diagnosed as "amnestic disorder due to a general medical condition" according to DSM-IV.

The term "attention deficit disorder," as used herein, refers to at disorder that is most commonly exhibited by children and which can be characterized by increased motor activity and a decreased attention span. The DSM-IV criteria can be used to diagnose attention deficit disorder.

The terms "D-serine" and "D-alanine" refer to the D isomers of the amino acids serine and alanine, respectively. As D isomers, rather than L isomers, these amino acids are not naturally found in proteins.

"Negative" symptoms of schizophrenia include affect blunting, anergia, alogia and social withdrawal, which can be measured using SANS (the Scales for the Assessment of Negative Symptoms; see Andreasen (1983) *Scales for the Assessment of Negative Symptoms* (SANS), Iowa City, Iowa).

"Positive" symptoms of schizophrenia include delusion and hallucination, which can be measured using PANSS (Positive and Negative Syndrome Scale; see Kay et al. (1987) *Schizophrenia Bulletin* 13: 261-276).

"Cognitive" symptoms of schizophrenia include impairment in obtaining, organizing, and using intellectual knowledge which can be measured by the Positive and Negative Syndrome Scale-cognitive subscale (PANSS-cognitive subscale) (Lindenmayer et al. (1994) *J. Nerv. Ment. Dis.* 182: 631-638) or with cognitive tasks such as the Wisconsin Card Sorting Test and battery of Measurement and Treatment Research to Improve Cognition in Schizophrenia (MATRICS, "www.matrics.ucla.edu/matrics-psychometrics-frame.htm").

A "full" agonist of the NMDA receptor is a compound that produces a maximal response at full receptor occupancy.

A "partial" agonist of the NMDA receptor is a compound that produces a lower maximal response at full receptor occupancy than do full agonists.

A "glycine uptake inhibitor of the NMDA receptor" is a compound that inhibits the re-uptake of glycine and increases the availability of glycine for the NMDA receptor (e.g., N-methylglycine).

The phrase "in conjunction with" when used in reference to the use of one or more drugs (active agents) described herein indicates that the drug(s) and the active agent(s) are administered so that there is at least some chronological overlap in their physiological activity on the organism. Thus the active agent(s) can be administered simultaneously and/or sequentially. In sequential administration there may even be some substantial delay (e.g., minutes or even hours or days) before administration of the second moiety as long as the first administered drug/agent has exerted some physiological alteration on the organism when the second administered agent is administered or becomes active in the organism.

The phrase "enhancing the in vivo activity" or "enhancing the apparent activity" when referring to the agents described herein indicates that the agents, when administered in conjunction with a pharmaceutical produce a greater biological response in the organism than the same dosage administered without the agent.

The term mammal includes essentially any mammal including, but not limited to dogs, cats, sheep, cattle, horses, goats, mice, rats, rabbits, hamsters, pigs, monkeys and other non-human primates, and humans. Thus, veterinary as well as medical applications of this invention are contemplated.

"Ataxia" is a neurological sign and symptom consisting of gross lack of coordination of muscle movements.

"Spinocerebellar degeneration" refers to a group of genetic disorders characterized by slowly progressive incoordination of gait and often associated with poor coordination of hands, speech, and eye movements. Frequently, atrophy of the cerebellum occurs. As with other forms of ataxia, results in unsteady and clumsy motion of the body due to a failure of the fine coordination of muscle movements, along with other symptoms.

"Parkinson's disease" belongs to a group of chronic and progressive conditions called movement disorders. It is characterized by muscle rigidity, tremor, a slowing of physical movement (bradykinesia) and, in extreme cases, a loss of physical movement (akinesia). The primary symptoms are the results of decreased stimulation of the motor cortex by the basal ganglia, normally caused by the insufficient formation and action of dopamine, which is produced in the dopaminergic neurons of the brain. Secondary symptoms may include high level cognitive dysfunction and subtle language problems.

"Obsessive compulsive disorder" is a mental disorder most commonly characterized by a intrusive, repetitive thoughts resulting in compulsive behaviors and mental acts that the person feels driven to perform, according to rules that must be applied rigidly, aimed at preventing some imagined dreaded event; however, these behaviors or mental acts are not connected to the imagined dreaded event. Patients can be diagnosed as having obsessive compulsive disorder using the DSMIV criteria.

Generalized anxiety disorder (GAD) is an anxiety disorder that is characterized by excessive, uncontrollable and often irrational worry about everyday things that is disproportionate to the actual source of worry. This excessive worry often interferes with daily functioning, as individuals suffering GAD typically anticipate disaster, and are overly concerned about everyday matters such as health issues, money, death, family problems, friend problems or work difficulties. They often exhibit a variety of physical symptoms, including fatigue, fidgeting, headaches, nausea, numbness in hands and feet, muscle tension, muscle aches, difficulty swallowing, bouts of difficulty breathing, trembling, twitching, irritability, sweating, insomnia, hot flashes, and rashes. Patients can be diagnosed as suffering from GAD by using the DSM-IV criteria.

Panic disorder is an anxiety disorder characterized by recurring severe panic attacks. It may also include significant behavioral change lasting at least a month and of ongoing worry about the implications or concern about having other attacks. The latter are called anticipatory attacks. Patients can be diagnosed as suffering from panic disorder by using the DSM-IV criteria.

Phobia is an intense and persistent fear of certain situations, activities, things, animals, or people. The main symptom of this disorder is the excessive and unreasonable desire to avoid the feared subject. When the fear is beyond one's control, and if the fear is interfering with daily life, then a diagnosis under one of the anxiety disorders can be made. Patients can be diagnosed as suffering from phobia by using the DSM-IV criteria.

Social Phobia is anxiety (emotional discomfort, fear, apprehension, or worry) about social situations, interactions with others, and being evaluated or scrutinized by other people. It occurs early in childhood as a normal part of the development of social functioning, but may go unnoticed until adolescence or may surface in adulthood. People vary in how often they experience social anxiety and in which kinds of situations. Patients can be diagnosed as suffering from social phobia by using the DSM-IV criteria.

"Substance abuse", the disorder is characterized by a pattern of continued pathological use of a medication, non-medically indicated drug or toxin, that results in repeated adverse social consequences related to drug use, such as failure to meet work, family, or school obligations, interpersonal conflicts, or legal problems. The substance can be, but not limited to: Alcohol, Amphetamine (or amphetamine-like), *Cannabis*, Cocaine, Hallucinogen, Inhalant, Nicotine, Opioid, Phencyclidine (or phencyclidine-like), Sedative, hypnotic, or anxiolytic or Polysubstance dependence. Patients can be diagnosed as substance abuse using the DSMIV criteria (APA, 1994, Diagnostic and Statistical Manual of Mental Disorders (Fourth Edition), Washington, D.C.). When an individual persists in use of alcohol or other drugs despite problems related to use of the substance. Compulsive and repetitive use may result in tolerance to the effect of the drug and withdrawal symptoms when use is reduced or stopped. This, along with Substance Abuse are considered Substance Use Disorders The substance can be, but not limited to: Alcohol, Amphetamine (or amphetamine-like), *Cannabis*, Cocaine, Hallucinogen, Inhalant, Nicotine, Opioid, Phencyclidine (or phencyclidine-like), Sedative, hypnotic, or anxiolytic or Polysubstance dependence. Substance dependence can be diagnosed with physiological dependence, evidence of tolerance or withdrawal. Patients can be diagnosed as substance dependence using the DSMIV criteria (APA, 1994, Diagnostic and Statistical Manual of 30 Mental Disorders (Fourth Edition), Washington, D.C.).

A "neuropharmaceutical" refers to a drug used to treat neuropsychiatric, neuropsychological, or nervous-system disorders including, but not limited to depression, schizophrenial, bipolar disorder, attention deficit hyperactivity disorder (ADHD), schizophrenia, Alzheimer's disease, and the like.

Where Markush groups are indicated herein (e.g., "where x is selected from the group consisting of A, B, and C") subgroups are contemplated comprising any one or more of the elements making up the Markush group (e.g., A and B, A and C, B and C, A alone, B alone, C alone, for Markush Group A, B, and C).

DETAILED DESCRIPTION

Figure 1:
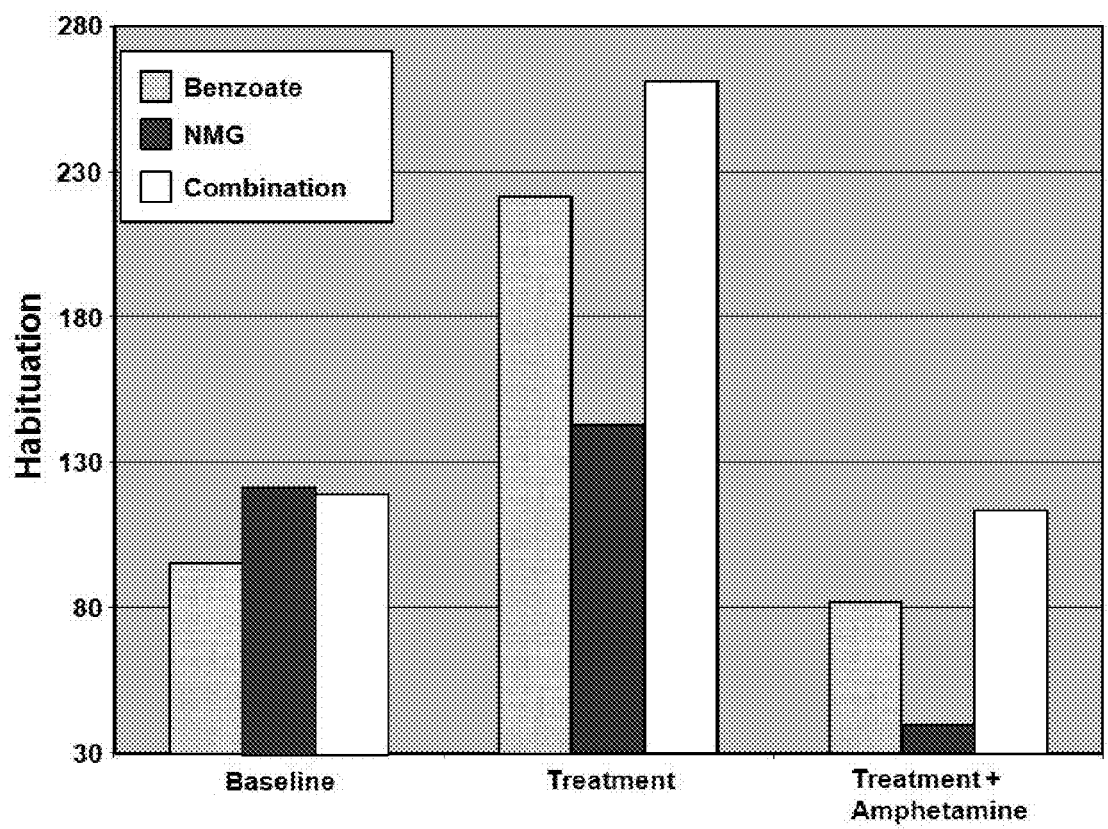
FIG. 1. The difference of startle responses between the initial and the last group of trials of single acoustic stimulus were considered the amount of habituation. Three groups of mice each were treated with sarcosine (200 mg/kg), benzoate (100 mg/kg), a combination of both sarcosine and benzoate. Amphetamatine (10 mg/kg) was administered 30 minutes before the experiments. There was no difference in the habituation at baseline across the groups (left group). Combination treatments (right) induce a stronger habituation effect than benzoate (left) or sarcosine treatment alone (middle). However, the effect of benzoate is close to the effect seen in the combination treatment. The same trend of habituation (combination treatment>benzoate>sarcosine) was evident when amphetamine was administered and disrupted the habituation (right group). The combination treatment corrected the amphetamine-induced disruption of habituation back to a normal state while single treatment of NMG or benzoate only partially corrected the deficit (right group). The effect of benzoate, however, was better than sarcosine and close to that seen in the combination treatment.

In various embodiments methods are provided for treating a patient diagnosed as suffering from a neuropsychiatric disorder or at high risk for a neuropsychiatric disorder, particularly a disorder characterized by a deficit in neurotransmission via the NMDA receptor (e.g., schizophrenia, bipolar disorder, Alzheimer's Disease, dementia, mild cognitive impairment, autism, Asperger's disorder, depression, benign forgetfulness, childhood learning disorders, close head injury, and attention deficit disorder, ataxia, spinocerebellar degeneration, Parkinson's disease, obsessive compulsive disorder (OCD), phobia, social phobia, substance abuse, and substance dependence). As described above, a variety of methods for diagnosing these disorders are known to those of skill in the art of clinical psychiatry, and any conventional diagnostic method can be used in conjunction with the invention.

In various embodiments this the compositions and methods described herein pertain to the use of "combination" therapies, where the subjects are administered a combination of one or more neuropharmaceuticals (e.g., an antipsychotic, an antidepressant, a phsychostimulant, a mood stabilizer, an anxiolytic, an Alzheimer's disease therapeutic, other psychotropics), and/or an NMDA (N-methyl-D-aspartate)-Enhancer, and/or a glycine transporter inhibitor, and/or a D-amino Acid Oxidase Inhibitor (DAAOI). In certain embodiments the combination therapy comprises a combination of an NMDA (N-methyl-D-aspartate)-Enhancer, and/or a Glycine Transporter Inhibitor, and/or a DAAOI inhibitor. In certain embodiments the administration of at least two of these agents in conjunction with each other is contemplated, and in certain embodiments, the administration of all three agents in conjunction with each other is contemplated. In various embodiments the agents can be utilized individually as well.

It was also a surprising discovery that DAAOI inhibitors (especially sorbic acid and/or benzoic acid and derivatives thereof) when used individually or in combination with each other are capable of mitigating one or more symptoms of a neuropsychiatric disorder. In addition, they are capable of enhancing the activity of neuropharmaceuticals (e.g., antipsychotics, antidepressants, ADHD medications, etc.). Accordingly, in certain embodiments, compositions that provide a prophylactically or therapeutically active amount of benzoic acid, a benzoic acid salt, a benzoic acid ester, or other benzoic acid derivative, and/or sorbic acid, a sorbic acid salt, a sorbic acid ester, or other sorbic acid derivative are provided. In various methods such compositions can be used for the treatment of a neuropsychiatric disorder and/or for the manufacture for a medicament for the treatment of a neuropsychiatric disorder.

In certain other embodiments, methods are contemplated that provided for the use of one or more D-amino Acid Oxidase Inhibitors in conjunction with one or more neuropharmaceuticals. In this regard, in certain preferred embodiments, the DAAOI comprises benzoic acid, a benzoic acid salt, a benzoic acid ester, or other benzoic acid derivative, and/or sorbic acid, a sorbic acid salt, a sorbic acid ester, or other sorbic acid derivative. Similarly, compositions comprising a combination of benzoic acid, a benzoic acid salt, a benzoic acid ester, or other benzoic acid derivative, and/or sorbic acid, a sorbic acid salt, a sorbic acid ester, or other sorbic acid derivative, and a neuropharmaceutical (e.g., an antipsychotic, an antidepressant, an ADHD medication, etc.) are contemplated. In addition kits comprising of benzoic acid, a benzoic acid salt, a benzoic acid ester, or other benzoic acid derivative, and/or sorbic acid, a sorbic acid salt, a sorbic acid ester, or other sorbic acid derivative are contemplated. In various embodiments the DAAOI and the neuropharmaceutical can be provided in separate containers. In certain embodiments the DAAOI and the neuropharmaceutical can be provided in the same container (e.g., as a combined/compound formulation).

Previous treatments using an NMDA enhancer or a glycine transporter inhibitor alone have had limited efficacy. It was discovered that the use of a DAAOI alone, especially a benzoic acid, benzoic acid salt, benzoic acid ester or other benzoic acid derivative and/or sorbic acid, a sorbic acid salt, a sorbic acid ester or other sorbic acid derivative can result in unexpected and surprising improvement in subjects diagnosed with a neuropsychiatric disorders. Accordingly in certain embodiments, the use of a benzoic acid salt, or other derivative and/or a sorbic acid, salt, or other derivative in the treatment of a neuropsychiatric disorder (e.g., schizophrenia, bipolar disorder, Alzheimer's disease, dementia, autism, Asperger's disorder, depression, benign forgetfulness, mild cognitive impairment, childhood learning disorders, close head injury, ataxia, spinocerebellar degeneration, Parkinson's disease, general anxiety disorder, panic disorder, obsessive compulsive disorder, phobia including social phobia, substance abuse, substance dependence, attention deficit disorder, etc.) are contemplated. Similarly medicaments comprising a benzoic acid, benzoic acid salt, benzoic acid ester or other benzoic acid derivative and/or sorbic acid, a sorbic acid salt, a sorbic acid ester or other sorbic acid derivative in an amount sufficient to mitigate one or more symptoms of a neuropsychiatric disorder are contemplated.

In addition, it was discovered that combination treatment(s), e.g., a benzoic acid, benzoic acid salt, benzoic acid ester or other benzoic acid derivative and/or sorbic acid, a sorbic acid salt, a sorbic acid ester or other sorbic acid derivative in combination with one or more neuropharmaceuticals, results in unexpected and surprising improvement in subjects diagnosed with a neuropsychiatric disorders. Thus methods comprising the administration of benzoic acid, a benzoic acid salt, a benzoic acid ester, or other benzoic acid derivative, and/or sorbic acid, a sorbic acid salt, a sorbic acid ester, or other sorbic acid derivative, in conjunction with one or more neuropharmaceuticals are contemplated. Similarly medicaments comprising a benzoic acid, benzoic acid salt, benzoic acid ester or other benzoic acid derivative and/or sorbic acid, a sorbic acid salt, a sorbic acid ester or other sorbic acid derivative and one or more neuropharmaceuticals (e.g., agents for the treatment of a condition such as schizophrenia, bipolar disorder, Alzheimer's disease, dementia, autism, Asperger's disorder, depression, benign forgetfulness, mild cognitive impairment, childhood learning disorders, close head injury, ataxia, spinocerebellar degeneration, Parkinson's disease, general anxiety disorder, panic disorder, obsessive compulsive disorder, phobia including social phobia, substance abuse, substance dependence, attention deficit disorder, etc.) are contemplated. Typically, the benzoic acid, benzoic acid salt, benzoic acid ester, or other benzoic acid derivative, and/or sorbic acid, sorbic acid salt, sorbic acid ester, or other sorbic acid derivative, is provided in the method or medicament in an amount sufficient to enhance the efficacy of the neuropharmaceutical.

Without being bound to a particular theory, it is believed that the DAAOI enhances the levels of both D-serine and D-alanine which are agonists of NMDA receptor and have been shown by the inventor to be beneficial for patients with schizophrenia and other disorders. It can help a wide variety of patients with cognitive impairment and other mental or behavioral symptoms. The combination therapies boost the NMDA and/or neuropharmaceutical activity and benefit subjects more than single agent treatments (e.g., antipsychotic drug, antidepressant, anxiolytic, mood stabilizer, psychotropic medication for attention deficit and hyperactivity disorder, drug for dementia, and the like).

Accordingly, in certain preferred embodiments, "combination" therapies are contemplated, where the subjects are administered a benzoic acid, a benzoic acid salt, a benzoic acid ester, or another benzoic acid derivative, and/or a sorbic acid, a sorbic acid salt, sorbic acid ester, or another sorbic acid derivative, in conjunction with a neuropharmaceutical (e.g., a therapeutic agent selected from the group consisting of an antipsychotic, an antidepressant, a phsychostimulant, a mood stabilizer, an anxiolytic, an Alzheimer's disease therapeutic, and/or other psychotropic for the treatment of a neuropsychiatric disorder).

In certain embodiments (e.g., for the treatment of schizophrenia, bipolar disorder, and the like) the neuropharmaceutical used in the "combination" treatment is an antipsychotic drug. In certain embodiments the antipsychotic drug is a drug selected from the group consisting of butyrophenone (e.g., Haloperidol (HALDOL®), phenothiazine (e.g., chlorpromazine (THORAZINE®), fluphenazine (PROLIXIN®), perphenazine (TRILAFON®), prochlorperazine (COMPAZINE®), thioridazine (MELLARIL®), trifluoperazine (STELAZINE®), mesoridazine, promazine, triflupromazine (VESPRIN®), levomepromazine (NOZINAN®), promethazine (PHENERGAN®), thioxanthene (e.g., chlorprothixene, flupenthixol (DEPIXOL®, FLUANXOL®), thiothixene (NAVANE®), zuclopenthixol (CLOPIXOL®, ACUPHASE®), clozapine (CLOZARIL®), olanzapine (ZYPREXA®), risperidone (RISPERDAL®, RISPERDAL CONSTA®), quetiapine (SEROQUEL®), ziprasidone (GEODON®), amisulpride (SOLIAN®), asenapine, paliperidone, Aripiprazole (ABILIFY®), dopamine partial agonists (BIFEPRUNOX®, NORCLOZAPINE® (ACP-104)), lamotrigine (LAMICTAL®), memantine (AXURA®, AKATINOL®, NAMENDA®, EBIXA®, ABIXA®), tetrabenazine (NITOMAN®, XENAZINE®), cannabidiol, LY2140023, and the like).

In certain embodiments (e.g., for the treatment of depression, panic disorder, social phobial, GAD, etc.) the neuropharmaceutical used in the "combination treatment" comprises an antidepressant and/or mood stabilizer. In certain embodiments the antidepressant comprises a monoamine oxidase inhibitor (MAOI), a tricyclic antidepressant (TCA), a tetracyclic antidepressant (TeCA), a selective serotonin reuptake inhibitor (SSRI), a noradrenergic and specific serotonergic antidepressant (NASSA), a norepinephrine (noradrenaline) reuptake inhibitor, a norepinephrine-dopamine reuptake inhibitor, and/or a serotonin-norepinephrine reuptake inhibitor (SNRI).

In certain embodiments the antidepressant is a drug selected from the group consisting of a tricyclic antidepressant (e.g., IMIPRAMINE® and variants), a selective serotonin reuptake inhibitor (SSRI) (e.g., fluoxetine (PROZAC®), paroxetine (PAXIL®, SEROXAT®), escitalopram (LEXAPRO®, ESIPRAM®), citalopram (CELEXA®), sertraline (ZOLOFT®), fluvoxamine (LUVOX®)), a serotonin-norepinephrine reuptake inhibitor (SNRI) (e.g., venlafaxine (EFFEXOR®)), milnacipram and duloxetine (CYMBALTA®), a noradrenergic and specific serotonergic antidepressant (NASSA) (e.g., mirtazapine (AVANZA®, ZISPIN®, REMERON®), mianserin), a norepinephrine (noradrenaline) reuptake inhibitor (NRI) (e.g., reboxetine (EDRONAX®)), a norepinephrine-dopamine reuptake inhibitors (e.g., bupropion (WELLBUTRIN®, ZYBAN®)), Amitriptyline, Nortriptiline, Protriptyline, Desipramine, Trimipramine, Amoxapine, Bupropion, Bupropion SR, S-Citalopram, Clomipramine, Desipramine, Doxepin, Isocarboxazid, Velafaxine XR, Tranylcypromine, Trazodone, Nefazodone, Phenelzine, Lamatrogine, Lithium, Topiramate, Gabapentin, Carbamazepine, Oxacarbazepine, Valporate, Maprotiline, Mirtazapine, Brofaromine, Gepirone, Moclobemide, isoniazid, iproniazid, and the like.

In certain embodiments (e.g., for the treatment of ADD or ADHD), the neuropharmaceutical used in the "combination treatment" comprises an agent for the treatment of ADD and/or ADHD. In certain suitable ADHD medications include, but are not limited to an ADHD medication selected from the group consisting of Statins Amphetamine, Modafinil, Desoxyn, Methamphetamine, cocaine, arecoline, Dexmethylphenidate (Focalin, Focalin XR), dextroamphetamine (Dexedrine, Dexedrine Spansules, Dextroamphetamine ER, Dextrostat), methylphenidate (Concerta, Daytrana, Metadate CD, Metadate ER, Methylin, Methylin ER, Ritalin, Ritalin-LA, Ritalin-SR), lisdexamfetamine dimesylate (Vyvanse), mixed salts amphetamine (Adderall, Adderall XR), Atomoxetine (Strattera), clonidine hydrochloride (Catapres), guanfacine hydrochloride (Tenex), arecoline, and Pemoline.

In certain embodiments (e.g., for the treatment of a cognitive disorder, and/or a condition characterized by neurodegeneration (e.g. Alzheimer's disease, Parkinson's disease, etc.)) the neuropharmaceutical used in the "combination treatment" can include, but is not limited to an agent selected from the group consisting of Donepezil, Tacrine, Rivastigmine, memantine (AXURA®, AKATINOL®, NAMENDA®, EBIXA®, ABIXA®), aricept, physostigmine, nicotine, arecoline, huperzine alpha, selegiline, Rilutek® (riluzole), vitamine c, vitamine e, carotenoids, *ginkgo biloba*, and the like.

In various embodiments the benzoic acid, benzoic acid salt, or derivative thereof, and/or sorbic acid, a sorbic acid salt, or a derivative thereof, can be administered separately before, after, or simultaneously with one or more the neuropharmaceuticals. For example, the benzoic acid, benzoic acid salt, or derivative thereof, and/or sorbic acid, a sorbic acid salt, or a derivative thereof can be provided in one formulation and the neuropharmaceutical(s) in another formulation.

In certain embodiments where the benzoic acid, benzoic acid salt, or derivative thereof, and/or sorbic acid, a sorbic acid salt, or a derivative thereof is administered simultaneously with the neuropharmaceuticals they can be provided as a combined formulation. Accordingly, in certain embodiments, corresponding combination therapeutics are also provided. Thus, in certain embodiments, a pharmaceutical composition is provided comprising a benzoic acid, benzoic acid salt, benzoic acid ester, or other benzoic acid derivative and/or sorbic acid, a sorbic acid salt, a sorbic acid ester, or other sorbic acid derivative and a neuropharmaceutical (e.g, an antidepressant, an anxiolytic, an antipsychotic drug, etc.), where the benzoic acid, benzoic acid salt, benzoic acid ester, or other benzoic acid derivative and/or sorbic acid, a sorbic acid salt, a sorbic acid ester, or other sorbic acid is present in an amount sufficient to increase the efficacy of neuropharmaceutical (e.g., risperidone, olanzapine, etc.). Also provided are formulations comprising a benzoic acid, benzoic acid salt, or derivative thereof (e.g., a benzoate, and/or sorbic acid, sorbic acid salt, or a derivative thereof (e.g., a sorbate); and an antidepressant drug, where the benzoic acid, benzoic acid salt, or derivative thereof, and/or thereof, and/or sorbic acid, sorbic acid salt, or a derivative thereof, is present in a concentration sufficient to increase the efficacy of the antidepressant drug (e.g., sertraline hydrochloride, fluoxetine hydrochloride, etc.).

Also provided are formulations comprising the benzoic acid, benzoic acid salt, benzoic acid ester, or other benzoic acid derivative, and/or sorbic acid, sorbic acid salt, sorbic acid ester, or other sorbic acid derivative, and a neuropharmaceutical e.g., as described above. Typically, the benzoic acid, benzoic acid salt, benzoic acid ester, or other benzoic acid derivative, and/or sorbic acid, sorbic acid salt, sorbic acid ester, or other sorbic acid derivative, is present in an amount sufficient to increase the efficacy of the neuropharmaceutical (e.g., Aricept, memantine, etc.).

In certain embodiments the combination formulation for the treatment of schizophrenia, bipolar disorder, and the like comprises a combination of benzoic acid, benzoic acid salt, benzoic acid ester, or other benzoic acid derivative, and/or sorbic acid, sorbic acid salt, sorbic acid ester, or other sorbic acid derivative and an antipsychotic drug. Suitable antipsychotic drugs include, but are not limited to the antipsychotic drugs described above.

In certain embodiments the combination formulation for the treatment of schizophrenia, bipolar disorder, and the like comprises a combination of depression, panic disorder, social phobial, GAD, and the like comprises a combination of benzoic acid, benzoic acid salt, benzoic acid ester, or other benzoic acid derivative, and/or sorbic acid, sorbic acid salt, sorbic acid ester, or other sorbic acid derivative and an antidepressant and/or mood stabilizer. Suitable antidepressants and mood stabilizers include, but are not limited to the antidepressants and mood stabilizers described above.

In certain embodiments the combination formulation for the treatment of ADD and/or ADHD, and the like comprises a combination of benzoic acid, benzoic acid salt, benzoic acid ester, or other benzoic acid derivative, and/or sorbic acid, sorbic acid salt, sorbic acid ester, or other sorbic acid derivative and an agent for the treatment of ADD and/or ADHD. Suitable agents for the treatment of ADD and/or ADHD include, but are not limited to the agents for the treatment of ADD and/or ADHD described above.

In certain embodiments the combination formulation for the treatment of a cognitive disorder, and/or a condition characterized by neurodegeneration (e.g. Alzheimer's disease, Parkinson's disease, etc.) comprises a combination of benzoic acid, benzoic acid salt, benzoic acid ester, or other benzoic acid derivative, and/or sorbic acid, sorbic acid salt, sorbic acid ester, or other sorbic acid derivative and an agent for the treatment of a cognitive disorder, and/or a condition characterized by neurodegeneration. Suitable agents for the treatment of a cognitive disorder, and/or a condition characterized by neurodegeneration include, but are not limited to the agents for the treatment of a cognitive disorder, and/or a condition characterized by neurodegeneration described above.

Typically, in various embodiments, the benzoic acid, benzoic acid salt, or derivative thereof (e.g., a benzoate), and/or sorbic acid, a sorbic acid salt, or a derivative thereof, is present in an amount sufficient to enhance therapeutic efficacy of the neuropharmaceutical rather than as a preservative, and/or melting point lowering agent, and/or stabilizer, and/or a lubricant, and/or a stabilizer, etc. In effect, the benzoic acid, benzoic acid salt, or derivative thereof, and/or sorbic acid, sorbic acid salt, or a derivative thereof, is an active agent. Thus, in various embodiments the benzoic acid, benzoic acid salt, benzoic acid ester, or other benzoic acid derivative, and/or sorbic acid, sorbic acid salt, sorbic acid ester, or other sorbic acid derivative, is not substantially present as an acid addition salt of the neuropharmaceutical (or at least the majority of the benzoic or sorbic acid or derivative thereof) is not present as an acid salt addition salt of the neuropharmaceutical. Similarly, in certain embodiments the benzoic acid, benzoic acid salt, benzoic acid ester, or other benzoic acid derivative, and/or sorbic acid, sorbic acid salt, sorbic acid ester, or other sorbic acid derivative, (or at least the majority of the benzoic or sorbic acid or derivative thereof) is not present as a co-crystal of the neuropharmaceutical.

In certain compositions, and treatments, the ratio of benzoic acid, benzoic acid salt, benzoic acid ester, or other benzoic acid derivative, and/or sorbic acid, sorbic acid salt, sorbic acid ester, or other sorbic acid derivative, to neuro-pharmaceutical (e.g., antidepressant, antipsychotic drug, therapeutic for attention deficit and hyperactivity disorder, therapeutic for dementia, and/or mood stabilizer, or other pharmaceutical) is stoichiometrically greater than 2:1, preferably greater than about 3:1, 4:1, 5:1, 6;1, 7:1, 8:1, 9;1, 10:1, 15:1, or 20:1. In certain embodiments the benzoic acid, benzoic acid salt, benzoic acid ester, or other benzoic acid derivative, and/or sorbic acid, sorbic acid salt, sorbic acid ester, or other sorbic acid derivative, combinations expressly exclude a psychoactive pharmaceutical other than an antipsychotic and/or antidepressant and/or therapeutic for attention deficit and hyperactivity disorder and/or therapeutic for dementia.

In various embodiments the benzoic acid, benzoic acid salt, benzoic acid ester, or other benzoic acid derivative, and/or sorbic acid, sorbic acid salt, sorbic acid ester, or other sorbic acid derivative is typically provided in an amount sufficient to improve the therapeutic efficacy of the neuropharmaceutical (e.g, antipsychotic and/or antidepressant and/or therapeutic for attention deficit and hyperactivity disorder and/or therapeutic for dementia). Thus, typical dosages of the benzoic acid, benzoic acid salt, benzoic acid ester, or other benzoic acid derivative, and/or sorbic acid, sorbic acid salt, sorbic acid ester, or other sorbic acid derivative, range from range is from about 5 mg, to about 500 grams, more preferably about 25 mg to about 400, 300 grams, 200 grams, or 100 grams, still more preferably about 50 mg to 50 or to 100 or 150 grams.

Most of the neuropsychiatric disorders present with cognitive deficits, behavioral and mental symptoms. The various treatment strategies described herein can be applied to most if not all of them including, for example, learning disorder, attention deficit and hyperactivity disorder, schizophrenia, bipolar disorder, depression, Alzheimer's Disease, autism, benign forgetfulness, close head injury, dementia, mild cognitive impairment, ataxia, spinocerebellar degeneration, Parkinson's disease, obsessive compulsive disorder (OCD), phobia, social phobia, generalized anxiety disorder (GAD), panic disorder, substance abuse, and substance dependence. In addition to their benefits for human subjects, the treatments described herein can be used in veterinary applications (e.g., to canines, felines, equines, bovines, porcines, etc.) with treatment of household pets (e.g., canine, feline) being of considerable interest. In addition, the combination treatments described herein can improve cognition in animal models of learning and model of schizophrenia, depression, anxiety, and the like.

In certain embodiments the treatment methods of the invention entail administering to a subject in need thereof (e.g., a patient diagnosed as having or at risk for a neuropsychiatric disorder) one or more a pharmaceutical compositions containing a therapeutically effective amount(s) of (i) an NMDA (N-methyl-D-aspartate)-Enhancer, and/or (ii) a glycine transporter inhibitor, and/or (iii) a D-amino Acid Oxidase Inhibitor (DAAOI). Where combinations of two or all three of these agents are utilized they can be administered separately (simultaneously or sequentially), in a single "combination" formulation, or in simultaneously or sequentially a combination formulation comprising two agents and a second formulation comprising a single agent.

The effective doses of the active agent(s) (of an NMDA (N-methyl-D-aspartate)-Enhancer, and/or Glycine Transporter Inhibitor, and/or D-amino Acid Oxidase Inhibitor (DAAOI)) can vary, depending upon factors such as the condition of the patient, the severity of the symptoms of the disorder, and the manner in which the pharmaceutical composition is administered. In various embodiments, for human patients, the effective unit dose of typical compounds include: DAAOI (e.g., benzoate, range of 50 mg-150 grams), NMDA enhancers (D-serine, range of 50 mg-50 grams; D-alanine, range 1-150 grams), glycine transporter inhibitor (for example: sarcone, range 50 mg-50 grams); including DAAOI+NMDA enhancer, DAAOI+glycine transporter inhibitor, NMDA enhancers+glycine transporter inhibitor or three classes of compound together.

In various embodiments, then, effective doses of each of the active agent(s) ranges from 1 mg, 10 mg, 50 mg, 100 mg, 250 mg, or 500 mg, 300 g, 200 g, 150 g, 100 g, 50 g, 25 g, 10 g, 5 g, or 1 g depending of factors including, but not limited to 150 g. In certain embodiments the compounds and compositions of the present invention can be administered to a patient at dosage levels in the range of about 0.1 to about 1,000 mg per day. For a normal human adult having a body weight of about 70 kilograms, it is estimated that a dosage in the range of about 0.01 to about 100 mg per kilogram of body weight per day is sufficient. The specific dosage used, however, can vary. For example, the dosage can depend on a numbers of factors including the requirements of the patient, the severity of the condition being treated, and the pharmacological activity of the compound being used. The determination of optimum dosages for a particular patient is well-known to those skilled in the art. The amount of active ingredient(s) that may be combined with the carrier materials to produce a single dosage form will vary depending upon the host treated and the particular mode of administration. It will be understood, however, that the specific dose level for any particular patient will depend upon a variety of factors including the activity of the specific compound(s) employed, the age, body weight, general health, sex, diet, time of administration, route of administration, and rate of excretion, drug combination and the severity of the particular disease undergoing therapy.

In all of the methods of the invention, appropriate dosages of the active agent(s) can readily be determined by those of ordinary skill in the art of medicine by monitoring the patient for signs of disease amelioration or inhibition, and increasing or decreasing the dosage and/or frequency of treatment as desired.

In various embodiments an amount equivalent to a dosage of about 10 mg to about 50 g/day, more preferably about 10 mg to about 10 g/day is administered to a patient in need of such treatment. For example, the dosage can be in an amount of 10 mg, 50 mg, 100 mg, 200 mg, 300 mg, such as 150 to 300 mg (e.g., 175 mg, 200 mg, 225 mg, or 250 mg).

Generally, treatment continues for at least one week and can continue for several years or life-long as needed to control the subject's symptoms.

Administration and Formulations.

In various embodiments the pharmaceutical compositions can be administered to the subject (e.g., patient) by any, or a combination, of several routes, such as oral, intravenous, trans-mucosal (e.g., nasal, vaginal, etc.), pulmonary, transdermal, transnasal, ocular, buccal, sublingual, intraperitoneal, intrathecal, intramuscular, or long term depot preparation. In certain embodiments solid compositions for oral administration can contain suitable carriers or excipients, such as corn starch, gelatin, lactose, acacia, sucrose, micro-crystalline cellulose, kaolin, mannitol, dicalcium phosphate, calcium carbonate, sodium chloride, lipids, alginic acid, or ingredients for controlled slow release. Disintegrators that can be used include, without limitation, micro-crystalline cellulose, corn starch, sodium starch glycolate and alginic acid. Tablet binders that can be used include, without limitation, acacia, methylcellulose, sodium carboxymethylcellulose, polyvinylpyrrolidone (Povidone), hydroxypropyl methylcellulose, sucrose, starch, and ethylcellulose.

In various embodiments liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the patient to be treated.

In certain embodiments injectable compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, the compounds may be administered by the drip method, whereby a pharmaceutical composition containing the active compound(s) and a physiologically acceptable excipient is infused. Physiologically acceptable excipients may include, for example, 5% dextrose, 0.9% saline, Ringer's solution or other suitable excipients. For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil. Alternatively, the pharmaceutical composition can be formulated as a chewing gum, lollipop, or the like.

In various embodiments combined formulations are contemplated. In certain embodiments such formulations contain at least two of the following three active agent(s): (i) an NMDA (N-methyl-D-aspartate)-Enhancer, and/or (ii) a glycine transporter inhibitor, and/or (iii) a D-amino Acid Oxidase Inhibitor (DAAOI). In certain embodiments all three active agent(s) are present in a single formulation. In combined formulations the different components can be segregated, for example, in different layers of a tablet, in different microbeads/microcapsules, and the like. In certain embodiments two of more of the active agents are intermixed and/or suspended, e.g., in a single excipient. Typically the different active agent(s) will be provided each in a therapeutically effective dose.

D-Amino Acid Oxidase Inhibitor (DAAOI)

Many D-amino Acid Oxidase Inhibitors (DAAOIs) suitable for use in the methods of the present invention are well known to those of skill in the art. Suitable DAAO inhibitors include, for example, but are not limited to benzoic acid and derivatives, sorbic acid and derivatives, 2-oxo-3-pentynoate; Aminoguanidine (Guanylhydrazine; Carbamimidic hydrazide; Pimagedine; GER 11; Hydrazinecarboximidamide) or hydrochloride salt (Guanylhydrazine hydrochloride), bicarbonate salt, nitrate salt, sulfate (2:1) salt, sulfate (1:1) salt, and hemisulfate salt thereof; benzoic acid; sodium benzoate; 2-aminobenzoate; 3-aminobenzoate; 4-aminobenzoate (p-aminobenzoate, PABA, Vitamin Bx, Vitamin H1); Methylglyoxal bis(guanylhydrazone) (also known as: Methyl GAG; Mitoguazone; 1,114(methylethanediylidene)dinitrilo) diguanidine; Hydrazinecarboximidamide, 2,2'-(1-methyl-1, 2-ethanediylidene)bis-; Pyruvaldehyde bis(amidinohydrazone); Megag; Mitoguazona [INN-Spanish]; Guanidine, 1,1$^1$-((methylethanediylidene)dinitrilo)di-; 1,1$^1$-((Methylethanediylidene)dinitrilo)diguanidine); Methylglyoxal bis (guanylhydrazone), dihydrochloride; phenylglyoxal bis(guanylhydrazone) (PhGBG); glyoxal bis(guanylhydrazone) (GBG; Guanidine, 1,11-(ethanediylidenedinitrilo)di(8C1); Hydrazinecarboximidamide, 2,2'-(1,2-ethanediylidene)bis-(9C1)); indole-propionic (IPA, 3-(3-Indolyl)propanoic acid); 3-indole-acetic acid (Heteroauxin, IAA); Indole-3-acetic acid Sodium salt; Indole-3-acetone; Indole-3-acetamide; Indole-3-acetyl-L-aspartic acid; Indole-3-acetyl-L-alanine; Indole-3-acetylglycine; Indole-3-acetaldehyde Sodium Bisulfite Addition compound; Indole-3-carboxylic acid; Indole-3-pyruvic acid (3-(3-Indolyl)-2-oxopropanoic acid); salicylic acid (2-Hydroxybenzoic acid); salicylic acid Sodium Salt; Salicylic acid Potassium Salt; Dansyl chloride (5-(Dimethylamino)naphthalene-1-sulfonyl chloride); Dansyl fluoride (5-(Dimethylamino)naphthalene-1-sulfonyl fluoride); dansyl glycine; Alanine tetrazole; benzoic tetrazole; tetrazole; Riboflavin 5'-pyrophosphate (RPP, 5-Phospho-alpha-D-ribosyl diphosphate, PRib-PP, P-RPP); DL-propargylglycine (DL-PG, 2-Amino-4-pentynoic acid); L-C-Propargylglycine; N-Acetyl-DL-propargylglycine; (±)-Sodium 3-hydroxybutyrate; Trigonelline Hydrochloride (1-Methylpyridinium-3-carboxylate); N-methylnicotinate; Methyl 6-methylnicotinate; Ethyl 2-methylnicotinate; Kojic acid (2-Hydroxymethyl-5-hydroxy-gamma-pyrone, 5-Hydroxy-2-hydroxymethyl-4-pyranone); derivatives of kojic acid, such as: 6-(pyrrolidinomethyl)-kojic acid hydrochloride, 6-(morpholinomethyl)-kojic acid, 6-(diethylaminomethyl)-kojic acid hydrochloride; O-(2,4-dinitrophenyl)hydroxylamine; 2,4-dinitrophenyl glycine; Hydroxylamine Hydrochloride; Methyl-p-nitrobenzenesulfonate (Methyl 4-nitrobenzenesulfonate); Aminoethylcysteine-ketimine (AECK, Thialysine ketimine, 2H-1,4-Thiazine-5,6-dihydro-3-carboxylic acid, S-Aminoethyl-L-cysteine ketimine, 2H-1,4-Thiazine-3-carboxylic acid, 5,6-dihydro-); 1,4-thiazine derivatives; 4-Phenyl-1,4-sulfonazan (Tetrahydro-4-phenyl-4H-1,4-thiazine 1-oxide, 4H-1,4-Thiazine, tetrahydro-4-phenyl-, 1-oxide); 1. Phenothiazine (Thiodiphenylamine, 10H-Phenothiazine, AFI-Tiazin, Agrazine, Antiverm, Dibenzo-1,4-thiazine); 3,4-Dihydro-2H-1, 4-thiazine-3,5-dicarboxylic acid (3,4-Dhtca, CAS#86360-62-5); Nifurtimox (Nifurtimox [BAN:INN], 1-((5-Nitrofurfurylidene)amino)-2-methyltetrahydro-1,4-thiazine-4,4-dioxide, 3-Methyl-4-(5$^1$-nitrofurylidene-amino)-tetrahydro-4H-1,4-thiazine-1,1-dioxide, BAY 2502, 4-((5-Nitrofurfurylidene)amino)-3-methylthiomorpholine 1,1-dioxide); 3-(1-Pyrrolidinylmethyl)-4-(5,6-dichloro-1-indancarbonyl)-tetrahydro-1,4-thiazine hydrochloride (R 84760; R 84761; Thiomorpholine, 4-((5,6-dichloro-2,3-dihydro-1Hinden-1-yl)carbonyl)-3-(1-pyrrolidinylmethyl)-, monohydrochloride, (R—(R*,S*))—); ketimine reduced forms; cystathionine; cystathionine ketimine; lanthionine ketimine; thiomorpholine-2-carboxylic acid; thiomorpholine-2,6-dicarboxylic acid; TMDA (1,4-Thiomorpholine-3, 5-dicarboxylic acid); 1-chloro-1-nitroethane; anthranilate; Ethyl 2-aminobenzoate (ethyl anthranilate); Methyl 2-aminobenzoate (Methyl anthranilate); picolinate; Ethyl picolinate (2-(Ethoxycarbonyl)pyridine, Ethyl 2-pyridinecarboxylate, L-Leucine methyl ester, hydrochloride; L-leucine ([(S)-(+)-leucine]); Fluorodinitrobenzene (1-Fluoro-2,4-dinitrobenzene, 2,4-DNFB, Benzene, 1-fluoro-2,4-dinitro-, VAN); Dinitrochlorobenzene (1-Chloro-2,4-dinitrobenzene, 1,3-Dinitro-4-chlorobenzene); 1,2-cyclohexanedione; Allylglycine (D-Allylglycine, 4-Pentenoic acid, 2-amino-); 2-amino-2,4-pentadienoate; 2-hydroxy-2,4-pentadienoate; 2-amino-4-keto-2-pentenoate; 2-hydroxybutyrate; Sodium 2-hydroxybutyrate; N-chloro-D-leucine; N-Acetyl-D-leucine; D-Leu (D-2-Amino-4-methylpentanoic acid); D-propargylglycine; 2-Amino-4-pentynoic acid; D,L-Propargylglycine; L-2-Amino-4-pentynoic acid; Progesterone (4-Pregnene-3,20-dione); FAD (Flavin adenine dinucleotide, 1H-Purin-6-amine, flavin dinucleotide, Adenosine 5'-(trihydrogen pyrophosphate), 5'-5'-ester with riboflavin); 6-OH-FAD; Phenylglyoxal (2,2-Dihydroxyacetophenone); Phenylglyoxal Monohydrate (2,2-Dihydroxyacetophenone monohydrate); Cyclothionine (Perhydro-1,4-thiazepine-3,5-dicarboxylic acid, 1,4-Hexahydrothiazepine-3,5-dicarboxylic acid, 1,4-Thiazepine-3,5-dicarboxylic acid, hexahydro-); alpha-alpha'-iminodipropionic (Alanopine; 2,21-Iminodipropionic acid; L-Alanine, N-(1-carboxyethyl)-); Meso-Diaminosuccinic acid (3-Aminoaspartic acid; Diaminosuccinic acid; CAS RN: 921-52-8); meso-2,3-Diaminosuccinic acid (CAS RN: 23220-52-2); Thiosemicarbazide (thiocarbamoyl hydrazide); Thiourea (Sulfourea; Thiocarbamide); Methylthiouracil (4(6)-Methyl-2-thiouracil, 4-Hydroxy-2-mercapto 6-methylpyrimidine); Sulphathiazole (N1-(2-Thiazolypsulfanilamide, 4-Amino-N-2-thiazolylbenzenesulfonamide); Sulfathiazole Sodium Salt (4-Amino-N-2-thiazolylbenzenesulfonamide sodium salt); thiocyanate; 3-methylbenzyl thiocyanate; methimazole (2-mercapto-1-methylimidazole, 1-methylimidazole-2-thiol); dicarboxylic hydroxyacids; 1,3-Acetonedicarboxylic acid (3-Oxoglutaric acid); D-tartaric acid ([(2S,3S)-(−)-tartaric acid, unnatural tartaric acid]); L-tartaric acid ([(2R,3R)-(+)-tartaric acid, natural tartaric acid]); DL-tartaric acid; potassium tartrate; D-malic acid; [(R)-(+)-malic acid, (R)-(+)-hydroxysuccinic acid]; L-malic acid; [(S)-(−)-malic acid, (S)-(−)-hydroxysuccinic acid]; DL-Malic acid (DL-hydroxysuccinic acid); Alpha-keto acids that are analogues of the amino acids alanine, leucine, phenylanaline, phenylglycine, tyrosine, serine, aspartate, and salts and derivatives thereof; pyruvic acid (2-Oxopropionic acid, alpha-Ketopropionic acid); sodium pyruvate; Pyruvic acid methyl ester (methyl pyruvate); Phenylpyruvic acid; Calcium phenylpyruvate (calcium pyruvate); Phenylpyruvic acid Sodium salt (Sodium phenylpyruvate); 4-hydroxyphenyl pyruvic acid; sodium alpha-ketoisovaleric acid (3-Methyl-2-oxobutyric acid sodium salt, 3-methyl-2-oxobutanoic acid sodium salt, α-Ketoisovaleric acid Sodium salt; Ketovaline Sodium salt); benzoylformic acid (α-Oxophenylacetic acid, Phenylglyoxylic acid); 4-methylthio-2-oxopentanoic acid; 4-Methyl-2-oxopentanoic acid (4-Methyl-2-oxovaleric acid; alpha-Ketoisocaproic acid; 4-methylthio-2-oxybutanoic acid; 2-oxybutanoic acid (hydroxybutyrate; 2-Hydroxybutyric acid; alpha-Hydroxy-n-butyric acid; DL-alpha-Hydroxybutyric acid Sodium Salt (sodium (±)-2-Hydroxybutyrate); Indole-3-pyruvic acid (alpha-Keto analogue of tryptophan); The reaction product between cysteamine and bromopyruvate; cysteamine (2-Aminoethanethiol; 2-Mercaptoethylamine); pantetheine; 5-adenosylmethionine; Ethyl bromopyruvate; Methyl bromopyruvate; Bromopyruvate; and 5-S-Cysteinyldopamine (see, e.g., PCT Publication WO 03/047558 and US Patent Publication No: 2003/0185754 A1).

Benzoic and Sorbic Acid Salts and Derivatives.

In certain embodiments preferred DAAOIs include, but are not limited to a benzoic acid, benzoic acid salt, benzoic acid ester and/or a derivative thereof, and/or sorbic acid, a sorbic acid salt, or a derivative thereof. Illustrative benzoic acid salts include, but are not limited to sodium benzoate, potassium benzoate, calcium benzoate, lithium benzoate, magnesium benzoate, zinc benzoate, and the like. In certain embodiments the benzoate is selected from the group consisting of benzoic acid; sodium benzoate; 2-aminobenzoate; 3-aminobenzoate; 4-aminobenzoate (p-aminobenzoate, PABA, Vitamin Bx, Vitamin H1, and benzo[d]isoxazol-3-ol derivatives (see, e.g., U.S. Pat. No. 7,166,725, PCT Publication WO 03/047558, and US Patent Publication No: 2003/0185754 A1 which are incorporated herein by reference), and the like. In certain embodiments the compounds discloses in U.S. Pat. No. 7,166,725, PCT Publication WO 03/047558, and US Patent Publication No: 2003/0185754 A1 are expressly excluded.

Illustrative sorbic acid (2,4-hexadienoic acid) salts include, but are not limited to sodium sorbate, potassium sorbate, calcium sorbate. Other sorbic acid derivatives include, but are not limited to sorbohydroxamic acid, sorbic aldehyde, sorbic acid-thiol adducts, 8-quinolinylsorbate, m-nitrosorbanilide, and the like.

NMDA Enhancer

NMDA enhancers suitable for use in certain methods of the present invention are well known to those of skill in the art. Suitable NMDA enhancers include, for example, but are not limited to D-alanine, a salt of D-alanine, an ester of D-alanine, an alkylated D-alanine, a precursor of D-alanine, D-serine, a salt of D-serine, an alkylated D-serine, a precursor of D-serine, D-cycloserine, a salt of D-cycloserine, an ester of D-cycloserine, a precursor of D-cycloserine, an alkylated D-cycloserine, N,N-dimethylglycine, a salt of N,N-dimethylglycine, an ester of N,N-dimethylglycine, an alkylated N,N-dimethylglycine, and N,N,N-trimethylglycine.

In certain embodiments the composition is substantially free of D-cycloserine when the agonist is D-alanine, a salt of D-alanine, an ester of D-alanine, an alkylated D-alanine, or a precursor of D-alanine; and when the agonist is D-cycloserine, a salt of D-cycloserine, an ester of D-cycloserine, a precursor of D-cycloserine, or alkylated D-cycloserine, the pharmaceutical composition comprises an amount of the agonist equivalent to 105-500 mg of D-cycloserine.

Glycine Transporter Inhibitor.

Glycine transporter inhibitors suitable for use in the methods of the present invention are well known to those of skill in the art. Suitable glycine transporter inhibitors include, but are not limited to sarcosine (N-methyl glycine), N-[3-(4'-fluorophenyl)-3-(4'-phenylphenoxy)propyl]sarcosine, (+)N[3-(4'-fluorophenyl)-3-(4'-phenylphenoxy)propyl]sarcosine (NFPS), pyridyl, pyridazinyl, pyrimidinyl and pyrazinyl piperidine compounds (see, e.g., WO/2005/094514, which is incorporated herein by reference, Pinard et al. (2008) Bioorg Med Chem Lett. 18(18): 5134-5139; Boulay et al. 92008) Pharmacol Biochem Behav. 91(1):47-58; Lindsley et al. (2006) Curr Top Med Chem. 6(17): 1883-1896; Depoortère et al. (2005) Neuropsychopharmacology 30(11): 1963-1985; Brown et al. (2001) Bioorg Med Chem Lett. 11(15): 2007-2009). Other glycine transporter inhibitors include, but are not limited to N-{3-[5-Cyano-1-(4-fluorophenyl)-1,3-dihydroisobenzofuran-1-yl]-1-propyl}glycine ethyl ester, N-{3-[5-Cyano-1-(4-fluorophenyl)-1,3-dihydroisobenzofuran-1-yl]-1-propyl}-N-methylglycine ethyl ester, N-{3-[5-Cyano-1-(4-fluorophenyl)-1,3-dihydroisobenzofuran-1-yl]-1-propyl}glycine, N-{3-[5-Cyano-1-(4-fluorophenyl)-1,3-dihydroisobenzofuran-1-yl]-1-propyl}-N-methylglycine, N-{3-[1-(3-chlorophenyl)-1,3-dihydroisobenzofuran-1-yl]-1-propyl}-N-methylglycine, N-{3-[1-(3-trifluoromethylphenyl)-1,3-dihydroisobenzofuran-1-yl]-1-propyl}-N-methylglycine, N-{3-[1-(3-trifluoromethylphenyl)-1,3-dihydroisobenzofuran-1-yl]-1-propyl}-N-methyl(1-ethyl) glycine, N-{3-[1-(4-methylphenyl)-1,3-dihydroisobenzofuran-1-yl]-1-propyl}-N-methylglycine, N-{3-[1-(4-fluorophenyl)-1,3-dihydroisobenzofuran-1-yl]-

1-propyl}-N-methylglycine, N-{3-[1-(4-fluorophenyl)-1,3-dihydroisobenzofuran-1-yl]-1-propyl}-N-methylalanine, N-{3-[1-(4-fluorophenyl)-1,3-dihydroisobenzofuran-1-yl]-1-propyl}-N-methyl(1-ethyl)glycine, N-{3-[4-chloro-1-(3-methyl-4-fluorophenyl)-1,3-dihydroisobenzofuran-1-yl]-1-propyl}-N-methylglycine, N-{3-[4-chloro-1-(4-chlorophenyl)-1,3-dihydroisobenzofuran-1-yl]-1-propyl}-N-methylglycine, N-{3-[5-chloro-1-(4-chlorophenyl)-1,3-dihydroisobenzofuran-1-yl]-1-propyl}-N-methylalanine, N-{3-[6-chloro-1-(3-methyl-4-fluorophenyl)-1,3-dihydroisobenzofuran-1-yl]-1-propyl}-N-methylglycine, N-{3-[6-chloro-1-(4-chlorophenyl)-1,3-dihydroisobenzofuran-1-yl]-1-propyl}-N-methylglycine, N-{3-[6-chloro-1-(4-methylphenyl)-1,3-dihydroisobenzofuran-1-yl]-1-propyl}-N-methylglycine, N-{3-[6-chloro-1-(4-methoxyphenyl)-1,3-dihydroisobenzofuran-1-yl]-1-propyl}-N-methylglycine, N-{3-[5-fluoro-1-(4-chlorophenyl)-1,3-dihydroisobenzofuran-1-yl]-1-propyl}-N-methylglycine, N-{3-[5-fluoro-1-(4-methoxyphenyl)-1,3-dihydroisobenzofuran-1-yl]-1-propyl}-N-methylglycine, N-{3-[5-trifluoromethyl-1-(4-fluorophenyl)-1,3-dihydroisobenzofuran-1-yl]-1-propyl}-N-methylglycine, N-{3-[5-trifluoromethyl-1-(4-fluorophenyl)-1,3-dihydroisobenzofuran-1-yl]-1-propyl}-N-methylalanine, N-{3-[5-cyano-1-(3-methyl-4-fluorophenyl)-1,3-dihydroisobenzofuran-1-yl]-1-propyl}-N-methylglycine, N-{3-[5-cyano-1-(4-cyanophenyl)-1,3-dihydroisobenzofuran-1-yl]-1-propyl}-N-methylalanine, N-{3-[5-cyano-1-(4-methoxyphenyl)-1,3-dihydroisobenzofuran-1-yl]-1-propyl}-N-methylglycine, N-{3-[5-cyano-1-(4-fluorophenyl)-1,3-dihydroisobenzofuran-1-yl]-1-propyl}-N-methylglycine, N-{2-[5-cyano-1-(4-fluorophenyl)-1,3-dihydroisobenzofuran-1-yl]ethyl}-N-methylglycine, N-{3-[5-Chloro-1-(4-chloro-phenyl)-indan-1-yl]-propyl}-N-methylglycine, N-{3-[5-Chloro-1-(4-chloro-phenyl)-indan-1-yl]-propyl}-N-methylalanine, N-{3-[3-cyclo-1-(4-methylphenyl)-1,3-dihydroisobenzofuran-1-yl]-1-propyl}-N-methylglycine, N-[3-(3,3-Dimethyl-1-phenyl-1,3-dihydro-benzo[c]thiophen-1-yl)-propyl]-N-methylglycine, N-[3-(3,3-Dimethyl-1-phenyl-1,3-dihydro-benzo[c]thiophen-1-yl)-propyl]-N-methylalanine, N-{3-[1-(4-Fluoro-phenyl)-3-dimethyl-1,3-dihydro-isobenzofuran-1-yl]-propyl}-Nmethylglycine, N-{3-[5-Bromo-1-(4-chlorophenyl)-1,3-dihydroisobenzofuran-1-yl]-1-propyl}-N-methylglycine, N-{2-[1-(4-Chloro-phenyl)-3,3-dimethyl-1,3-dihydro-isobenzofuran-1-yl]-ethyl}-N-methylglycine, N-[3-(3-methyl-1-phenyl-1H-inden-1-yl)-propyl]-N-methylglycine, N-[3-(5-Chloro-1-thiophen-2-yl-1,3-dihydro-isobenzofuran-1-yl)-propyl]-N-methylglycine, N-[3-(5-Chloro-1-thiophen-2-yl-1,3-dihydro-isobenzofuran-1-yl)-propyl]-N-methyl(1-ethyl)-glycine, N-[3-(3-methyl-1-phenyl-1,3-dihydro-isobenzofuran-1-yl)-propyl]-N-methylalanine, N-[3-(3-methyl-1-phenyl-1,3-dihydro-isobenzofuran-1-yl)-propyl]-N-methyl(1-ethyl)-glycine, N-[3-(3,3-Dimethyl-1-phenyl-1,3-dihydro-isobenzofuran-1-yl)-ethyl]-N-methylalanine, N-[3-(3,3-Dimethyl-1-(4-fluoro-phenyl)-1,3-dihydro-isobenzofuran-1-yl)-ethyl]-N-methylalanine, N-[3-(3,3-Dimethyl-1-phenyl-1,3-dihydro-isobenzofuran-1-yl)-ethyl]-N-methyl-(1-ethyl)glycine, N-[3-(3,3-Dimethyl-1-(4-fluoro-phenyl)-1,3-dihydro-isobenzofuran-1-yl)-ethyl]-N-methyl-(1-ethyl)glycine, N-[3-(3,3-Diethyl-1-phenyl-1,3-dihydro-isobenzofuran-1-yl)-propyl]-N-methyl alanine, N-[3-(3,3-Diethyl-1-(4-chloro-phenyl)-1,3-dihydro-isobenzofuran-1-yl)-propy l]-N-methylalanine, N-[3-(3,3-Diethyl-1-(4-chloro-phenyl)-1,3-dihydro-isobenzofuran-1-yl)-propyl]-N-methylglycine, N-[3-(1-phenyl-1,3-dihydro-benzo[c]thiophen-1-yl)-propyl]-N-methylalanine, N-{3-[1-(4-Chloro-phenyl)-3,3-dimethyl-indan-1-yl]-propyl}-N-methylglycine, N-{3-[1-(4-Chloro-phenyl)-3,3-diethyl-1,3-dihydro-isobenzofuran-1-yl]-propyl}-N-methyl-alanine, N-[2-(3-methyl-1-phenyl-indan-1-yl)-ethyl]-amino}-N-methylalanine, N-[3-(1-phenyl-(1H)-inden-1-yl)-propyl]-N-methylalanine, N-{3-[1-(4-Fluoro-phenyl)-5-(4-trifluoromethyl-phenyl)-1,3-dihydro-isobenzofuran-1-yl]-propyl}-N-methyl-glycine, N-{3-[5-Chloro-1-(4-chloro-phenyl)-indan-1-yl]-propyl}-N-methyl-glycine, N-{3-[5-Chloro-1-(4-chloro-phenyl)-indan-1-yl]-propyl}-N-methyl-alanine, N-{3-[1-(4-chloro-phenyl)-5-(4-trifluoromethyl-phenyl)-1,3-dihydro-isobenzofuran-1-yl]-ethyl}-N-methyl-glycine, N-{3-[1-(4-Chloro-phenyl)-5-(4-methyl-phenyl)-1,3-dihydro-isobenzofuran-1-yl]-ethyl}-N-methyl-glycine, N-{3-[1-(4-Chloro-phenyl)-5-(4-methoxy-phenyl)-1,3-dihydro-isobenzofuran-1-yl]-ethyl}-N-methyl-glycine, N-{3-[1-(4-Chloro-phenyl)-5-(2-thiophenyl)-1,3-dihydro-isobenzofuran-1-yl]-ethyl}-N-methyl-glycine, N-{3-[1-(4-Chloro-phenyl)-5-(4-methyl-phenyl)-1,3-dihydro-isobenzofuran-1-yl]-propyl}-N-methyl-glycine, N-{3-[1-(4-Chloro-phenyl)-5-(4-methoxy-phenyl)-1,3-dihydro-isobenzofuran-1-yl]-propyl}-N-methyl-glycine, N-{3-[1-(4-chloro-phenyl)-5-(4-trifluoromethyl-phenyl)-1,3-dihydro-isobenzo furan-1-yl]-propyl}-N-methyl-glycine, N-{3-[1-(4-Chloro-phenyl)-5-(4-chloro-phenyl)-1,3-dihydro-isobenzofuran-1-yl]-ethyl}-N-methyl-glycine, N-{2-[1-(4-Chloro-phenyl)-5-(5-chloro-thiophen-2-yl)-1,3-dihydro-isobenzofuran-1-yl]-ethyl}-N-methyl-glycine, N-{3-[1-(4-Chloro-phenyl)-5-(3-methyl-phenyl)-1,3-dihydro-isobenzofuran-1-yl]-ethyl}-N-methyl-glycine, N-{3-[1-(4-Chloro-phenyl)-5-(2-methyl-phenyl)-1,3-dihydro-isobenzofuran-1-yl]-ethyl}-N-methyl-glycine, N-{3-[1-(4-Chloro-phenyl)-5-(2,5-dichloro-phenyl)-1,3-dihydro-isobenzofuran-1-yl]-ethyl}-N-methyl-glycine, N-{3-[1-(4-chloro-phenyl)-5-(3-trifluoromethyl-phenyl)-1,3-dihydro-isobenzo furan-1-yl]-ethyl}-N-methyl-glycine, N-{3-[1-(4-chloro-phenyl)-5-(3-trifluoromethyl-phenyl)-1,3-dihydro-isobenzo furan-1-yl]-propyl}-N-methyl-glycine, N-{3-[1-(4-Chloro-phenyl)-5-(3,4-dichloro-phenyl)-1,3-dihydro-isobenzofuran-1-yl]-ethyl}-N-methyl-glycine, N-{3-[1-(4-Chloro-phenyl)-5-(4-chloro-phenyl)-1,3-dihydro-isobenzofuran-1-yl]-propyl}-N-methyl-glycine, N-{3-[1-(4-Chloro-phenyl)-5-(3-methyl-phenyl)-1,3-dihydro-isobenzofuran-1-yl]-propyl}-N-methyl-glycine, N-{3-[1-(4-Chloro-phenyl)-5-(2-methyl-phenyl)-1,3-dihydro-isobenzofuran-1-yl]-propyl}-N-methyl-glycine, N-{3-[1-(4-Chloro-phenyl)-5-(2,5-dichloro-phenyl)-1,3-dihydro-isobenzofuran-1-yl]-propyl}-N-methyl-glycine, N-{3-[1-(4-Chloro-phenyl)-5-(3,4-dichloro-phenyl)-1,3-dihydro-isobenzofuran-1-yl]-propyl}-N-methyl-glycine, and N-{3-[1-(4-chloro-phenyl)-5-(2-trifluoromethyl-phenyl)-1,3-dihydro-isobenzo furan-1-yl]-propyl}-N-methyl-glycine (see, e.g., U.S. Pat. No. 6,921,774, which is incorporated herein by reference), or other non glycine-, N-methylglycine-structurally based inhibitors (see, e.g., Harsing et al. (2006) *Current Medicinal Chemistry*, 13: 1017-1104).

Additional Active Agents.

In certain embodiments the methods can involve administering additional neuropharmaceuticals and other therapeutic agents instead of or in conjunction with the agents described above.

In certain embodiments such agents include, but are not limited to diazepam, bromazepam, prazepam, Chlordiazepoxide, Clobazam, Estazolam, Flurazepam, Clonazepam, Temazepam, Triazolam, Alprazolam, Midazolam, Brotizolam, Nitrazepam, Flunitrazepam, Oxazepam, Quazepam, Lorazepam, Temazepam, Triazolam, Zolpidem, Zopiclone, Zaleplon, Chlorpromazine, Thioridazine, Mesoridazine, Fluphenazine, Perphenazine, Trifluoperazine, Thiothixene, Haloperidol, Loxapine, Molindone, Clozapine, Risperidone, Olanzapine, Quetiapine, Haloperidol decanoate, Fluphenazine decanoate, Fluphenazine enanthate, Risperdal Consta, Amitriptyline, Amoxapine, Bupropion, Bupropion SR, Citalopram, S-Citalopram, Clomipramine, Desipramine, Doxepin, Duloxetine, Milnacipran, Fluoxetine, Fluvoxamine, Imipramine, Isocarboxazid, Lamatrogine, Lithium, Topiramate, Gabapentin, Carbamazepine, Oxacarbazepine, Valporate, Maprotiline, Memantine, Mirtazapine, Brofaromine, Gepirone, Moclobemide, Physostigmine, Nicotine, Huperzine Alpha, vitamine C, vitamine E, Carotenoids, *Ginkgo Biloba*, Statins, Nefazodone, Nortriptyline, Paroxetine, Phenelzine, Protriptyline, Sertraline, Protriptyline, Trimipramine, Amoxapine, isoniazid, iproniazid, venlafaxine, Velafaxine XR, mianserin, reboxetine, Selegiline, Tranylcypromine, Trazodone, Trimipramine, Venlafaxine, Velafaxine XR, Amphetamine, Modafinil, Desoxyn, Methamphetamine, arecoline, Dexmethylphenidate (Focalin, Focalin XR), dextroamphetamine (Dexedrine, Dexedrine Spansules, Dextroamphetamine ER, Dextrostat), methylphenidate (Concerta, Daytrana, Metadate CD, Metadate ER, Methylin, Methylin ER, Ritalin, Ritalin-LA, Ritalin-SR), lisdexamfetamine dimesylate (Vyvanse), mixed salts amphetamine (Adderall, Adderall XR), Atomoxetine (Strattera), clonidine hydrochloride (Catapres), guanfacine hydrochloride (Tenex), cocaine, Pemoline, Donepezil, Tacrine, Rivastigmine, Acetophenazine, Chlorprothixene, Droperidol, Pimozide, Butaperazine, Carphenazine, Remoxipride, Piperacetazine, Sulpiride, Ziprasidone, aripiprazole, Paliperidone, lamotrigine (LAMICTAL®), memantine (AXURA®, AKATINOL®, NAMENDA®, EBIXA®, ABIXA®), arecoline, acamprosate, tetrabenazine (XENAZINE®, NITOMAN®), RILUTEK® (riluzole), and the like.

Compound Formulations.

In certain embodiments, the agents described herein (e.g., benzoic acid, benzoic acid salt, or derivative thereof and/or sorbic acid, sorbic acid salt, or derivative thereof) and a neuropharmaceutical (e.g., as described herein) are administered separately, either simultaneously or sequentially. The agents are commercially available in suitable pharmaceutically acceptable formulations.

In certain embodiments, however, the agents e.g., benzoic acid, benzoic acid salt, benzoic acid ester, or other benzoic acid derivative and/or sorbic acid, sorbic acid salt, sorbic acid ester, or other sorbic acid derivative, and neuropharmaceutical (e.g., antidepressant, antipsychotic, phsychostimulant, mood stabilizers, anxiolytic, ADHD therapeutic, Alzheimer's disease therapeutic, and other psychotropics etc.) are provided as a combined formulations for administration by any of a variety of modalities including, but not limited to oral administration, rectal administration, injection, transdermal administration, subcutaneous depot administration, transnasal administration, and the like. Methods of preparing combined formulations are well known to those of skill in the art (see, e.g., Remington's Pharmaceutical Science, 15th ed., Mack Publishing Company, Easton, Pa. (1980), Remington: The Science and Practice of Pharmacy, 21st Ed. 2005, Lippincott Williams & Wilkins, and the like).

For example, for oral administration, the active agent(s) (e.g., benzoic acid, salt or derivative, and/or sorbic acid, salt, or derivative, and antipsychotic) can be combined with one or more excipients and used in the form of ingestible tablets, buccal tablets, troches, capsules, elixirs, suspensions, syrups, wafers, and the like. In wafer formulations, for example, different layers comprising the wafer can contain different agents. Similarly time-release capsules can comprise multiple active agents. Such compositions and preparations are typically formulated to deliver the desired concentration of agent(s) over the desired time period.

Similarly, for injectables, the active agents can be combined into a single injectable formulation.

Kits

In another embodiment this invention provides kits treating (e.g., mitigating one or more symptoms of) a neuropsychiatric disorder. The kits preferably comprise a container or containers containing the combinations of active agents described herein, either a separate formulations or as a single "combined" formulation. The agent(s) can be provided in a unit dosage formulation (e.g. suppository, tablet, caplet, patch, etc.) and/or may be optionally combined with one or more pharmaceutically acceptable excipients.

In certain embodiments the kits comprise benzoic acid, a benzoic acid salt, or a derivative thereof and/or sorbic acid, a sorbic acid salt, or a derivative thereof, and a neuropharmaceutical (e.g., an antipsychotic). The agents can be in separate containers or in the same container.

In addition, the kits optionally include labeling and/or instructional materials providing directions (i.e., protocols) for the practice of the methods or use of the "therapeutics" or "prophylactics" of this invention. Preferred instructional materials describe the use of combinations of agents as described herein to mitigate symptom(s) of a neuropsychiatric disorder and/or to prevent the onset or increase of one or more of such symptoms in an individual at risk for such a disorder. The instructional materials can also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Introduction

Treatment by the agents enhancing N-methyl-D-aspartate neurotransmission have gained attention as an alternative for patients not responding to available psychotropics including antipsychotic medication. However, the efficacy of the individual NMDA-enhancement is limited at typical dosages. We believe a combination of NMDA-enhancing agents will render better clinical efficacy than an individual agent alone. To evaluate this hypothesis, we applied the combinational strategy in the best accepted neurophysiological model of schizophrenia in rodents, startle habituation and prepulse inhibition (PPI).

The startle response is comprised of a constellation of reflexes elicited by sudden relatively intense stimuli. It offers many advantages as a behavioral measure of central nervous system activity when elicited by acoustic (noise burst), electrical (cutaneous), tactile (air puff), or visual (light flash) stimuli. The startle reflex has served as a tool for studying fundamental properties of nervous function of complex behavioral states and cognitive processes.

The forebrain modulates several forms of startle plasticity including the habituation and PPI. Changes in startle magnitude through repeated stimulus presentations-habituation and sensitization-represent the simple forms of learning. Quantification of startle habituation and sensitization in rodent has direct physiological relevance to human CNS function. In fact, the most well accepted animal physiology models for schizophrenia are startle habituation and PPI.

Therefore, to test the hypothesis that combinational NMDA-enhancing agent treatment has better efficacy than individual agent alone, we tested startle habituation and PPI in animals receiving single NMDA-enhancing agents, sarcosine (N-methylglycine, a glycine transporter-1 inhibitor), benzoate (a D-amino acid oxidase inhibitor), the combination of both agents or the vehicle. We also tested the hypothesis in a well accepted pharmacological model of schizophrenia, amphetamine-disruption of startle habituation and PPI.

Method

For the systematic investigation of the neurobiological systems that modulate sensorimotor inhibition, startle magnitude was investigated. Startle magnitude is reduced when the pulse stimulus is preceded 30 to 500 msec by a weak prepulse. This inhibition ("gating") of a motor response elicited by a weak sensory event, termed PPI, provides an operational measure of sensorimotor gating. Prepulse stimuli of 3, 6, or 12 dB above the 70 dB background noise inhibit the startle response elicited by 120-dB pulse stimuli. Prestimuli used in intramodal studies of sensorimotor gating of acoustic startle are by the delivery of a discrete acoustic prepulse several msec before the startle pulse, with an intensity below startle threshold. Holding the interval between the prepulse and pulse stimuli constant at 100 msec typically yields suitable levels of PPI, ranging from 20% to 80% inhibition.

For habituation, we present six trials of a single acoustic stimulus to each mouse. To provide a consistent acoustic environment and to mask external noises, maintain a continuous background noise level of 70 dB within each startle chamber. We collected the peak or average response from each mouse on each of six trials, then averaged the six responses together for each mouse. Five more trials at the end of PPI were done. The results were averaged and compared to the original six trials. The difference of startle responses between the initial six and the last five trials were considered the amount of habituation. Analyses include the independent variable (e.g., vehicle or drug treatment) as a factor in analyses of variance (ANOVA) on the dependent measures (difference of the average of the first and last six trials).

There were a total of 36 trials in the experiments. The three prepulse stimuli were with a duration of 20 msec. For each mouse the following metrics were determined: 1) Average response magnitude on pulse-only trials 1 to 6 and 32 to 36; 2) Average response magnitude in each of the four trial types between trials 7 and 31 inclusively (i.e., ten pulse-only trials and five each of the three prepulse variations). The first block of pulse-only trials were analyzed as measures of startle reactivity. The first and last blocks of pulse-only trials were analyzed together in a repeated measure ANOVA to assess habituation of acoustic startle across the test session. The four values (3, 6, or 12 dB above background) derived from trials 7 to 31 were used to assess PPI which was calculated for each mouse as: Percentage score: PPI=100%×{[pulse-only units−(prepulse+pulse units)]/(pulse-only units)}.

Male 129 SVE adult mice were first tested at baseline. Four groups of 10 mice each were treated with sarcosine (200 mg/kg), benzoate (100 mg/kg), a combination of both sarcosine and benzoate (same doses as the individual treatment), or with vehicle for one week before the test. The mice continued to receive the drug until one week later when amphetamatine (10 mg/kg) was administered 30 minutes before the experiments.

Results

We found that there was no difference in the habituation at baseline (when no drug had been administered) across the groups (FIG. 1, left group). But combination treatments induce a stronger habituation effect than benzoate or sarcosine treatment alone (FIG. 1, middle group). The effect of benzoate, however, was close to the combination treatment. The same trend of habituation (combination treatment>benzoate>sarcosine) was evident when amphetamine was administered and disrupted the habituation (FIG. 1, right group). The combination is better than the individual treatment in enhancing the habituation (FIG. 1, middle). The combination treatment corrected the amphetamine-induced disruption of habituation back to normal state while single treatment of NMG or benzoate partially correct the deficit (FIG. 1, right group). The effect of benzoate, however, is better than sarcosine and close to effect seen in the combination treatment.

Figure 2:
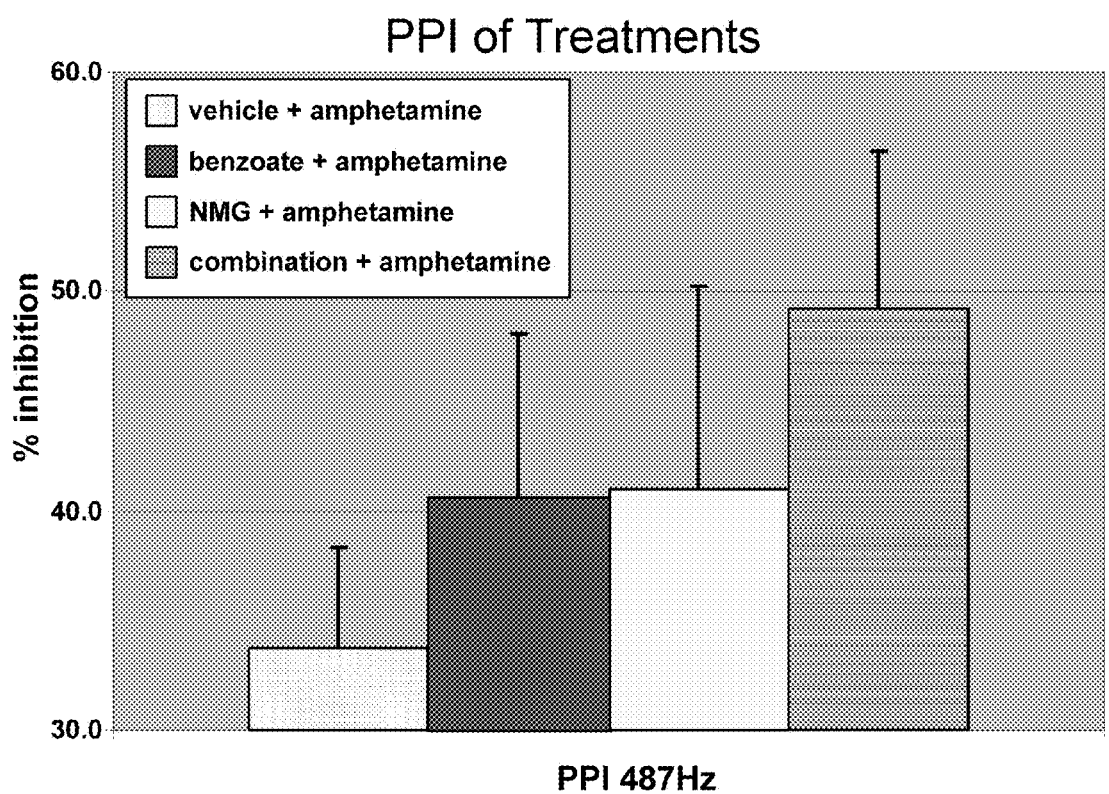
FIG. 2. Four groups of 10 mice each were treated with sarcosine (200 mg/kg), benzoate (100 mg/kg), a combination of both sarcosine and benzoate (same doses as the individual treatment), or with vehicle for one week before the test. The mice continued to receive the drug until one week later when amphetamatine (10 mg/kg) was administered 30 minutes before the experiments. For PPI, stronger prepulse inhibited pulse response more (inhibition of 525 Hz>487 Hz>468 Hz). Amphetamine disrupted the inhibition in all treatments. For example, in 487 Hz paradigm, the disruption by amphetamine is most pronounced in vehicle-treated mice (left column), partially corrected by either sarcosine (NMG) or benzoate (middle 2 columns) and was best corrected by the combination treatment (right column).

For PPI, we found that in general stronger prepulse inhibited pulse response more (inhibition of 525 Hz>487 Hz>468 Hz) (FIG. 2). Amphetamine disrupted the inhibition in all treatments. This disruption by amphetamine is most pronounced in vehicle treated mice (left column), partially corrected by either sarcosine (NMG) or benzoate (middle 2 columns) and was best corrected by the combination treatment (right column).

Conclusion

In the most accepted animal model of schizophrenia, which tests the sensory gating, we found that combination treatment improve the startle habituation and PPI significantly more than the individual agent alone. The effect of benzoate was close to combination treatment in habituation.

Example 2

Treatment of Schizophrenia by Sodium Benzoate, a D-Amino Acid Oxidase Inhibitor

Schizophrenia is a devastating mental disorder with high morbidity and mortality, affecting about 1% of the population worldwide. Furthermore, care for schizophrenia is extremely expensive in terms of direct and indirect costs. Clinical manifestation of schizophrenia consists of three domains: positive symptoms, negative symptoms, and neuropsychological deficits that are poorly addressed today.

Therapeutic Need for Schizophrenia—Beyond Clozapine

Pharmacotherapy of schizophrenia has been developed for half century. Conventional antipsychotics, which blockade majority of $D_2$ dopamine receptors only exerted effects on positive symptoms. Newer atypical antipsychotics targeting both dopamine $D_2$ and serotonin $5HT_2$ receptors have been suggested to be superior to conventional agents in terms of efficacy for positive symptoms, negative symptoms and cognitive deficits. Despite this, there were a considerable percentage of patients resistant or only partially responsive to available medications. Moreover, side-effect profiles of second-generation antipsychotic agents are significant, including hypotension, seizure, sedation, weight gain, hyperglycemia, diabetes mellitus, hyperlipidemia, and hematological abnormalities, limit their clinical use. Lastly, most schizophrenic patients still suffer from lifelong illness and deteriorating function.

Materials and Methods

Subjects

The research protocol was approved by the Institutional Review Boards (IRB) of the institute. Patients were screened and evaluated by the research psychiatrists. After complete description of the study to the subjects, written informed consent was obtained in line with the IRB's guidelines. The Structured Clinical Interview for DSM-IV was conducted for the diagnosis. Patients entered into this study if they 1) were physically healthy and had all laboratory assessments (including urine/blood routine, biochemical tests, and electrocardiograph) within normal limits, 2) aged 18-60 years, 3) satisfied DSM-IV criteria for schizophrenia (2), 4) had no DSM-IV diagnosis of substance (including alcohol) abuse or dependence, 5) consistently symptomatic without fluctuation and the antipsychotic doses were unchanged for at least 3 months, and 6) had a minimum baseline total score of 60 on the Positive and Negative Syndrome Scale (PANSS) (3).

Study Design

The dosing for the concurrent antipsychotics (all atypical antipsychotics), was an optimal dosing strategy which minimize side effects, especially extrapyramidal side effects (EPS), and can still yield favorable efficacy. After having achieved optimal treatment response, patients' antipsychotic doses remained constant for at least three months prior to the enrollment of the study and remained on the same antipsychotic regimens for the study period. All patients are treated with atypical antipsychotics, risperidone in majority.

All patients were then randomly assigned under double-blind conditions to receive a 6-week trial of placebo, or sodium benzoate (1 grams) daily. Patients were randomized in clusters of six subjects, without stratification, through a computer-generated randomization table to receive placebo or active drugs in a 1:1 ratio. To ensure concealment of the randomization assignment, study medication was provided in coded containers with supply of identical-appearing capsules of placebo or either of active compounds. The research pharmacist implemented random allocation and masked treatment assignment was communicated by telephone to research staff. Patients, caregivers, and investigators (except for the investigational pharmacist) were all masked to the assignment. Patient's compliance and safety were closely monitored by the research psychiatrists and the inpatient nursing staff.

Measures

The primary outcome measures were psychopathology changes measured by PANSS (3) and, Scales for the Assessment of Negative symptoms (SANS) (4) total scores, Quality of Life scale (10 items for inpatient use) (1, 5), and Global Assessment of Function (Axis V in DSM IV) (2). A secondary analysis aimed to explore whether the positive results (if any) from the PANSS or SANS were due to a general effect on all components or to an effect on a specific component(s).

Factor analyses for PANSS revealed 5 components: positive, negative, cognitive, depression and excitement (3). For the assessment of negative symptoms, we a priori chose SANS rather than PANSS-negative to avoid multiple comparisons because SANS is more comprehensive, consisted of five subscales: blunted affect, alogia, apathy, anhedonia/asociality, and attention (4). Nevertheless, we also presented the findings in the PANSS-negative component. Of the original 21 items on the Quality of Life scale (5), 10 (social activity, social initiatives, social withdrawal, sense of purpose, motivation, curiosity, anhedonia, aimless inactivity, capacity for empathy, emotional interaction) are selected for the inpatient setting (1). The Global Assessment of Function (GAF, Axis V in DSM IV) includes symptoms in the anchors (2). The GAF raters were instructed to ignore the symptom components.

Side-effect assessments included Simpson-Angus Rating Scale for EPS (6), Abnormal Involuntary Movement Scale (AIMS) for dyskinesia (7), and Barnes Akathesia Scale (8). Systemic side effects of treatments were evaluated by means of routine physical and neurological examinations, laboratory tests, and reviewed by applying the Udvalg for Kliniske Undersogelser (UKU) Side-effects Rating Scale (9).

Clinical ratings were performed by the research psychiatrists who were trained and experienced in the rating scales. Inter-rater reliability was analyzed with the ANOVA test. Only raters reaching the intraclass correlation coefficients of 0.90 or higher during pre-study training were allowed to rate the study patients. To maintain high interrater reliability and to prevent rater drift, raters met at least once a month for training and reliability re-testing. To minimize interrater variability, individual patients were assessed by the same research psychiatrist throughout the trial. Assessments were completed at baseline and at the end of weeks 2, 4, and 6.

Statistical Analysis

The demographic and clinical characteristics of the patients, antipsychotic doses, response rate, and side effects among groups were compared by Kruskal Wallis tests (or ANOVA tests if the distribution was normal) for continuous variables and by Chi-Square tests (or Fisher's Exact tests) for categorical variables.

We applied multiple linear regression with the generalized estimating equation (GEE) method (10) for the treatment by time (0, 2, 4, 6 weeks) interaction analysis, which simultaneously compared the treatment groups using a single analysis and allowed controlling for baseline psychopathology. The results of GEE models were analyzed by the SAS/STAT (SAS Institute Inc, Cary, N.C.) "PROC GENMOD" procedure with AR (autoregressive) (1) working correlation structure using the marginal model. Since there are three comparison groups, the placebo group was selected to be compared with the two active treatment groups. Because ANOVA and multiple linear regression can be applied only if the distribution of the response values is normal, we examined the distribution pattern using the "Kolmogorov D" package in SAS/INSIGHT v8.2. All hypothesis tests were two sided and conducted at the 0.05 alpha levels. To compare across the treatments, effect sizes between endpoint and baseline were calculated.

Results

Figure 3:
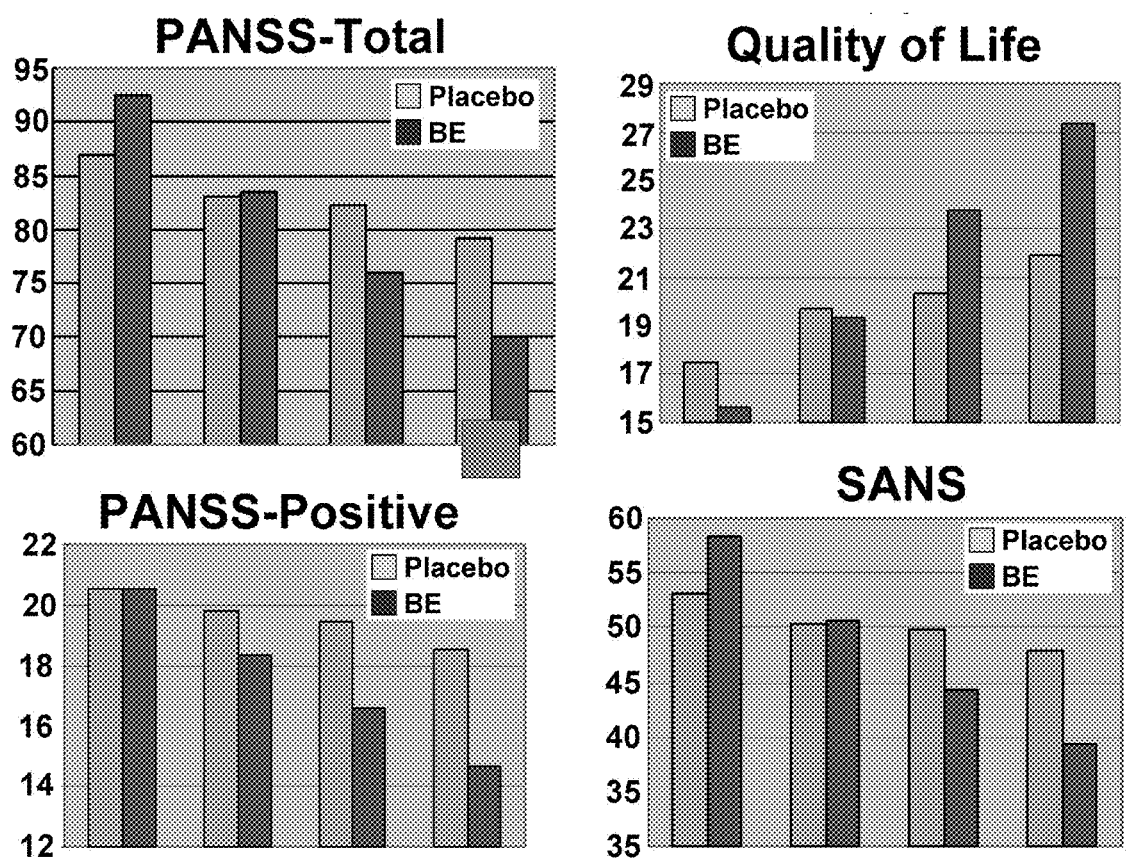
FIG. 3. Six weeks of adjunctive benzoate vs. placebo treatment in patients receiving risperidone treatment, at weeks 0, 2, 4, and 6, respectively. BE, benzoate, PANSS total, Positive and Negative Syndrome Scale total score; PANSS-positive, Positive and Negative Syndrome Scale-positive subscale score; SANS, Scales for the Assessment of Negative symptoms.

In this pilot, placebo-control, randomized, double blind trial (not yet published), we found that 1000-mg/day sodium benzoate adjunctive therapy (n=18) can significantly improve positive and negative symptoms and quality of life than placebo (n=18) in schizophrenia patients (FIG. 3). Benzoate also yielded good safety and tolerability. Treatment-emergent side effects were also similar between benzoate and placebo groups. These side effects were all mild, short-lived, and not warranting medical treatment.

We had optimized the treatment of schizophrenia by reconfirming the efficacy and safety of risperidone (ris)-benzoate combination (RBC). We found RBC was superior to risperidone (ris) (placebo add on) in all clinical domains, including cognitive function and life quality and its safety is equal to ris (placebo addon) treatment. This beneficial outcome will provide a new treatment for schizophrenia and markedly reduce the social cost for this severe mental disorder.

Example 3

Following acclimation at least 7 days in the animal facility prior to initiation of behavioral testing, the animals (rats) were subjected to the forced swim test (FST). The method of the FST has been used in previous animal studies of depression, which was modified by Cryan from the Porsolt's FST. (Porsolt et al, 1977; Cryan et al, 2002) The test was performed using a acrylic cylinder (diameter, 20 cm; height, 40 cm) filled to a height of 30 cm with 25° C. water. Rats were processed to a 15-min conditioning swim. Following 24 h after their first exposure, the rats were again placed in the swim apparatus for 5 min. The behavior of rats was observed 5 min after the administration of various drug treatments or 0.9% saline (control). All behavioral testing was conducted between 1600-1800 h. On the study day, the total periods of immobility during the 5-min testing period were recorded using the EthoVision Basic V 3.1 analysis program (Noldus, Wageningen, Netherlands). For the present experiment, the immobility threshold was set at 15% and a fixed averaging interval of 1 second was chosen to smooth the mobility parameter in EthoVision software. Below the immobile threshold, the animal is considered immobile. Using the settings, the activity of all rats was analyzed automatically and quantitatively for mobility and numbers of crossing vertical central line in the FST.

TABLE 1

Treatment effects for sodium benzoate and potassium sorbate in forced swim test.

|  | Vehicle | Sodium Benzoate (500 mg/kg) | Potassium Sorbate (500 mg/kg) |
| --- | --- | --- | --- |
| Immobility time (%) | 46.94 ± 4.6 | 40.17 ± 3.3 ($p < 0.05$) | 27.64 ± 6.2 ($p < 0.01$) |

The table indicates the scores on the behavioral scales of FST in three treatment groups. As can be seen, both sodium benzoate and potassium sorbate decrease the duration of immobility significantly as compared to the vehicle control group.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A pharmaceutical composition capable of mitigating at least one symptom associated with schizophrenia, comprising:
    500 milligrams to 10 grams of a first active ingredient, which is benzoic acid, or a benzoic acid salt; and
    an effective amount of a second active ingredient, which is risperidone, wherein the ratio of the first active ingredient to the second active ingredient is greater than 10:1, and wherein the pharmaceutical composition is in a solid dosage form.

2. The pharmaceutical composition according to claim 1, wherein the first active ingredient is a benzoic acid.

3. The pharmaceutical composition according to claim 1, wherein the first active ingredient is selected from the group consisting of benzoic acid, sodium benzoate, potassium benzoate, calcium benzoate, and lithium benzoate.

4. The pharmaceutical composition according to claim 1, wherein the ratio of the first active ingredient to the second active ingredient is greater than 15:1.

5. The pharmaceutical composition according to claim 1, wherein the ratio of the first active ingredient to the second active ingredient is greater than 20:1.

6. The pharmaceutical composition according to claim 1, wherein the first active ingredient is a benzoic acid salt, which is selected from the group consisting of sodium benzoate, potassium benzoate, calcium benzoate, and lithium benzoate.

7. The pharmaceutical composition according to claim 1, wherein the first active ingredient is sodium benzoate or lithium benzoate.

* * * * *